(12) United States Patent
Faries, Jr. et al.

(10) Patent No.: US 6,294,762 B1
(45) Date of Patent: Sep. 25, 2001

(54) WARMING SYSTEM AND METHOD FOR HEATING VARIOUS ITEMS UTILIZED IN SURGICAL PROCEDURES

(75) Inventors: Durward I. Faries, Jr., McLean; Bruce R. Heymann, Vienna; Calvin Blankenship, Centreville, all of VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 09/413,532

(22) Filed: Oct. 6, 1999

Related U.S. Application Data

(63) Continuation-in-part of application No. PCT/US98/06951, filed on Apr. 7, 1998.
(60) Provisional application No. 60/042,737, filed on Apr. 7, 1997.

(51) Int. Cl.[7] .............................. A61F 7/00; A61B 19/00
(52) U.S. Cl. ....................... 219/400; 126/21 A; 312/236; 222/146.5
(58) Field of Search ..................................... 219/385, 386, 219/394, 400, 428; 312/236; 604/114, 291; 222/146.5; 126/21 A; 34/209, 212, 215; 392/382

(56) References Cited

U.S. PATENT DOCUMENTS

| | | |
|---|---|---|
| 1,659,719 | 2/1928 | Blake . |
| 2,214,215 | 9/1940 | Watermann et al. . |
| 2,576,874 | 11/1951 | Acton . |
| 2,713,112 | 7/1955 | Mills et al. . |
| 2,741,099 | 4/1956 | Beane . |
| 2,885,526 * | 5/1959 | Paulding ............................. 219/385 |
| 2,994,760 | 8/1961 | Pecoraro et al. . |
| 3,051,528 | 8/1962 | Muckler et al. . |
| 3,241,603 | 3/1966 | Nagata . |
| 3,255,812 | 6/1966 | Bayane et al. . |
| 3,329,202 | 7/1967 | Birman . |
| 3,353,589 | 11/1967 | Tope et al. . |
| 3,386,498 | 6/1968 | Funfstuck . |
| 3,485,245 | 12/1969 | Lahr et al. . |
| 3,536,132 | 10/1970 | Pecoraro et al. . |

(List continued on next page.)

OTHER PUBLICATIONS

Cahill, New Name, New Helmsman, JEMS, Aug. 1996.
CBi Healthcare Systems, Inc., *Controlled Temperature Cabinet System*, JEMS, Mar. 1997.
Koolatron, P–34 PC–3 Precision Control Thermoelectric Cooler/Warmer, Jan. 1998.
Koolatron, Canadian company announces the release of a precision control unit, Aug. 1997.
Anton, 500 miles from nowhere, it'll give you a cold drink or a warm burger . . . , Technology Update, 1993.
Koolatron, 1997 U.S. $ Price List, 1997.
Kellow et al, Drug Adulteration in Prehospital Emergency Medical Services, Oct. 1994.
CBi Medical, Inc., IV Fluid Warmer Model 8362, 1992.

*Primary Examiner*—Joseph Pelham

(57) ABSTRACT

A surgical warming system heats medical items of various sizes, independently and simultaneously for immediate use. The warming system includes a plurality of compartments, each separately heated and controlled. The compartments may be modular and stackable, or multiple compartments of varying size may be formed into a single cabinet structure so as to receive different sized intravenous bags or bottles. Each compartment is heated by forcing a controlled mix of recycled and outside air through a heating chamber and then into the compartment. Each compartment includes a heating unit and controller allowing the simultaneous maintenance of different temperatures.

47 Claims, 9 Drawing Sheets

U.S. PATENT DOCUMENTS

| | | |
|---|---|---|
| 3,590,215 | 6/1971 | Anderson et al. . |
| 3,612,165 | 10/1971 | Haynes . |
| 3,713,302 | 1/1973 | Reviel . |
| 3,777,187 | 12/1973 | Kohn . |
| 3,826,305 | 7/1974 | Fishman . |
| 3,858,106 | 12/1974 | Launius . |
| 3,879,171 * | 4/1975 | Tulis ................................. 219/521 |
| 4,189,995 | 2/1980 | Löhr et al. . |
| 4,233,495 | 11/1980 | Scoville et al. . |
| 4,309,592 | 1/1982 | Le Boeuf . |
| 4,318,276 | 3/1982 | Sato et al. . |
| 4,328,676 | 5/1982 | Reed . |
| 4,364,234 | 12/1982 | Reed . |
| 4,407,133 | 10/1983 | Edmonson . |
| 4,419,568 * | 12/1983 | Overloop ............................ 219/386 |
| 4,455,478 * | 6/1984 | Guibert ............................... 219/400 |
| 4,464,563 | 8/1984 | Jewett . |
| 4,495,402 | 1/1985 | Burdick et al. . |
| 4,523,078 | 6/1985 | Lehmann . |
| 4,605,840 | 8/1986 | Koopman . |
| 4,657,004 | 4/1987 | Coffey . |
| 4,678,460 | 7/1987 | Rosner . |
| 4,707,587 | 11/1987 | Greenbalt . |
| 4,726,193 | 2/1988 | Burke et al. . |
| 4,745,248 | 5/1988 | Hayes . |
| 4,801,777 | 1/1989 | Auerbach . |
| 4,823,554 | 4/1989 | Trachtenberg et al. . |
| 4,874,033 | 10/1989 | Chatelain et al. . |
| 4,894,207 * | 1/1990 | Archer et al. ....................... 219/400 |
| 4,906,816 | 3/1990 | van Leerdam . |
| 4,910,386 * | 3/1990 | Johnson ............................... 219/385 |
| 4,935,604 | 6/1990 | Allen et al. . |
| 4,961,320 | 10/1990 | Gutmann . |
| 5,061,241 | 10/1991 | Stephens, Jr. et al. . |
| 5,061,630 | 10/1991 | Knopf et al. . |
| 5,081,697 | 1/1992 | Manella . |
| 5,106,373 | 4/1992 | Augustine et al. . |
| 5,108,372 | 4/1992 | Swenson . |
| 5,183,994 | 2/1993 | Bowles, Sr. et al. . |
| 5,195,976 | 3/1993 | Swenson . |
| 5,217,064 | 6/1993 | Kellow et al. . |
| 5,243,833 | 9/1993 | Coelho et al. . |
| 5,263,929 | 11/1993 | Falcone et al. . |
| 5,276,310 * | 1/1994 | Schmidt et al. ..................... 219/386 |
| 5,282,264 * | 1/1994 | Reeves et al. ...................... 219/385 |
| 5,297,234 | 3/1994 | Harms et al. . |
| 5,315,830 | 5/1994 | Doke et al. . |
| 5,333,326 | 8/1994 | Faries, Jr. et al. . |
| 5,345,923 | 9/1994 | Luebke et al. . |
| 5,364,385 | 11/1994 | Harms et al. . |
| 5,381,510 | 1/1995 | Ford et al. . |
| 5,397,875 | 3/1995 | Bechtold, Jr. . |
| 5,399,007 * | 3/1995 | Marconet ............................. 312/209 |
| 5,408,576 | 4/1995 | Bishop . |
| 5,483,799 | 1/1996 | Dalto . |
| 5,572,873 | 11/1996 | Lavigne et al. . |
| 5,653,905 | 8/1997 | McKinney . |
| 5,661,978 * | 9/1997 | Holmes et al. ....................... 62/3.6 |
| 5,729,653 | 3/1998 | Maglisochetti et al. . |
| 5,910,210 | 6/1999 | Violi et al. . |
| 5,924,289 | 7/1999 | Bishop, II . |
| 5,977,520 | 11/1999 | Madson, Jr. et al. . |
| 5,986,239 | 11/1999 | Corrigan, III et al. . |
| 6,124,572 * | 9/2000 | Spilger et al. ...................... 219/400 |

* cited by examiner

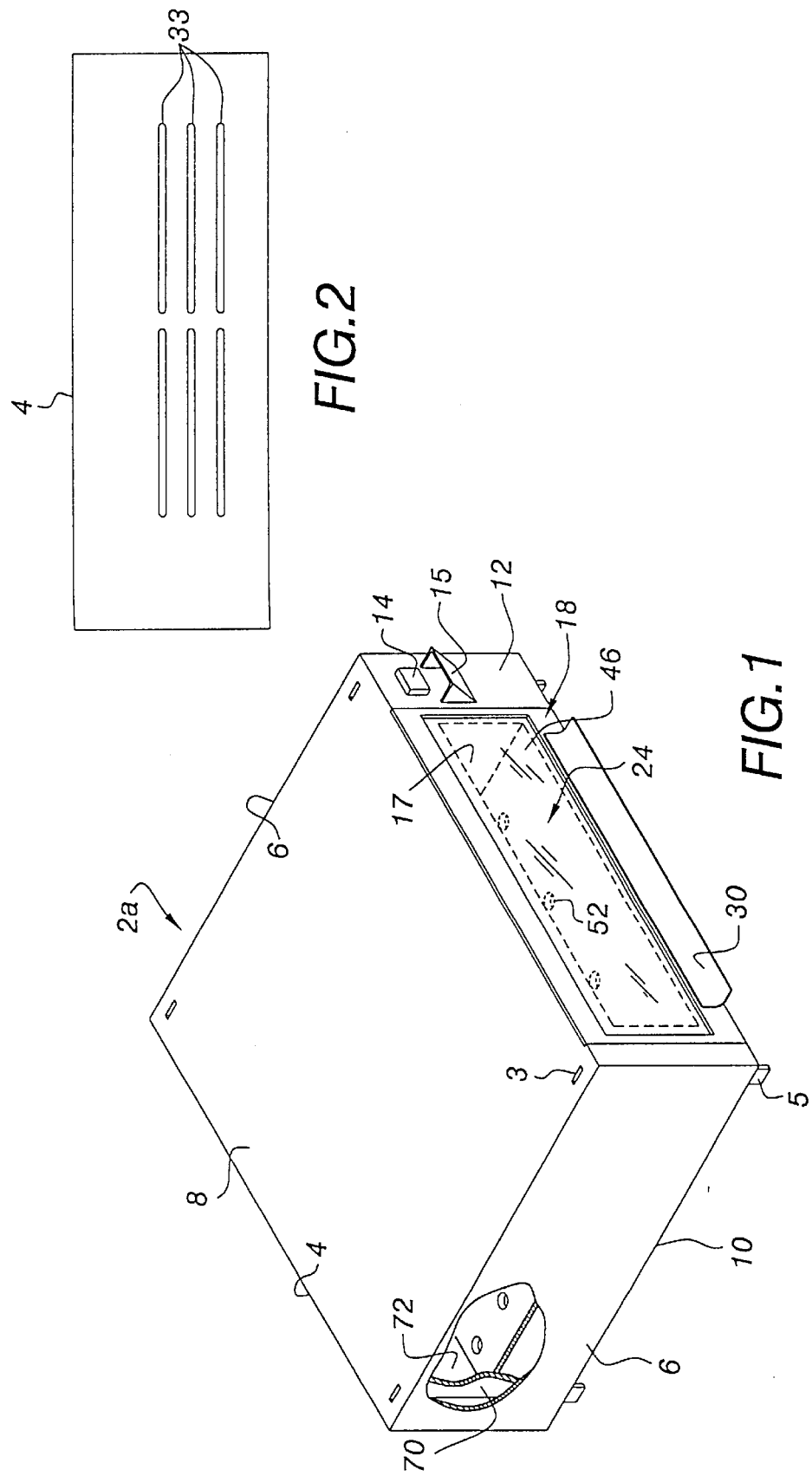

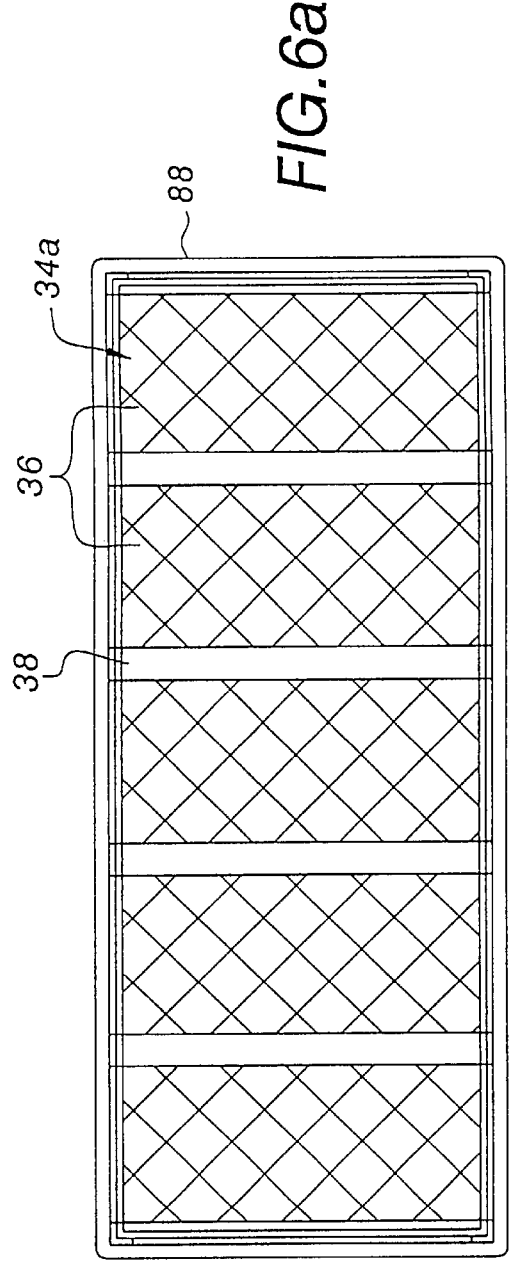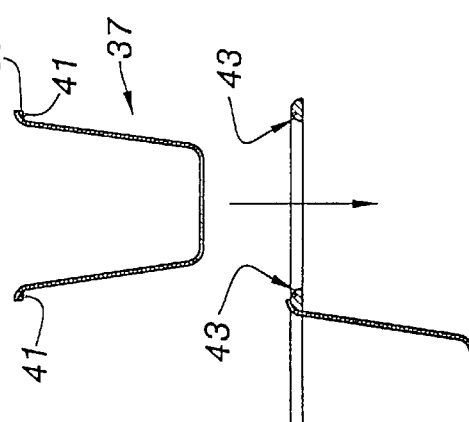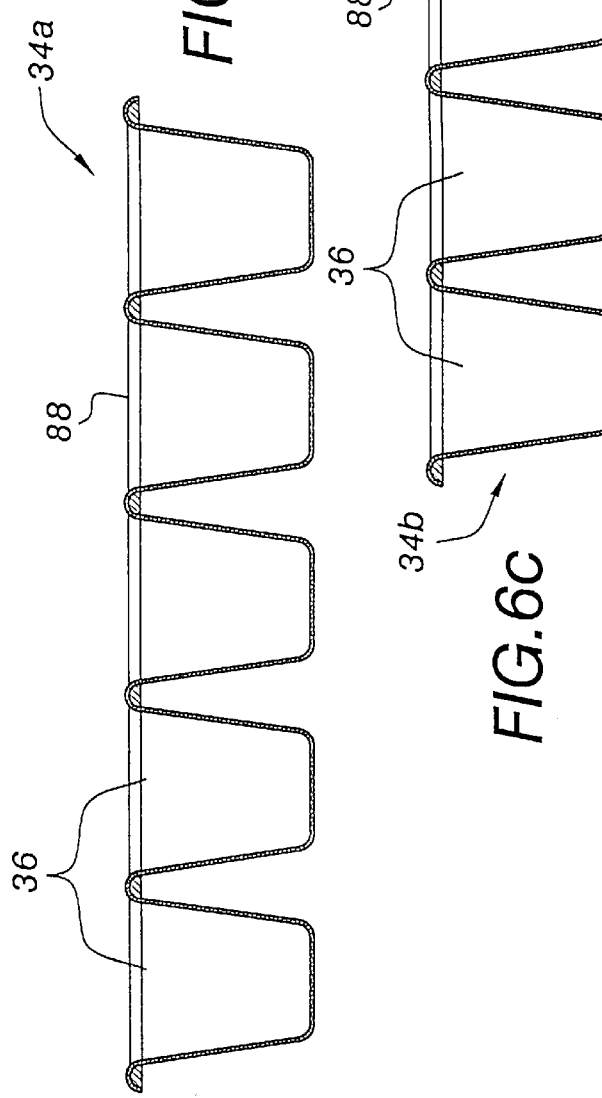

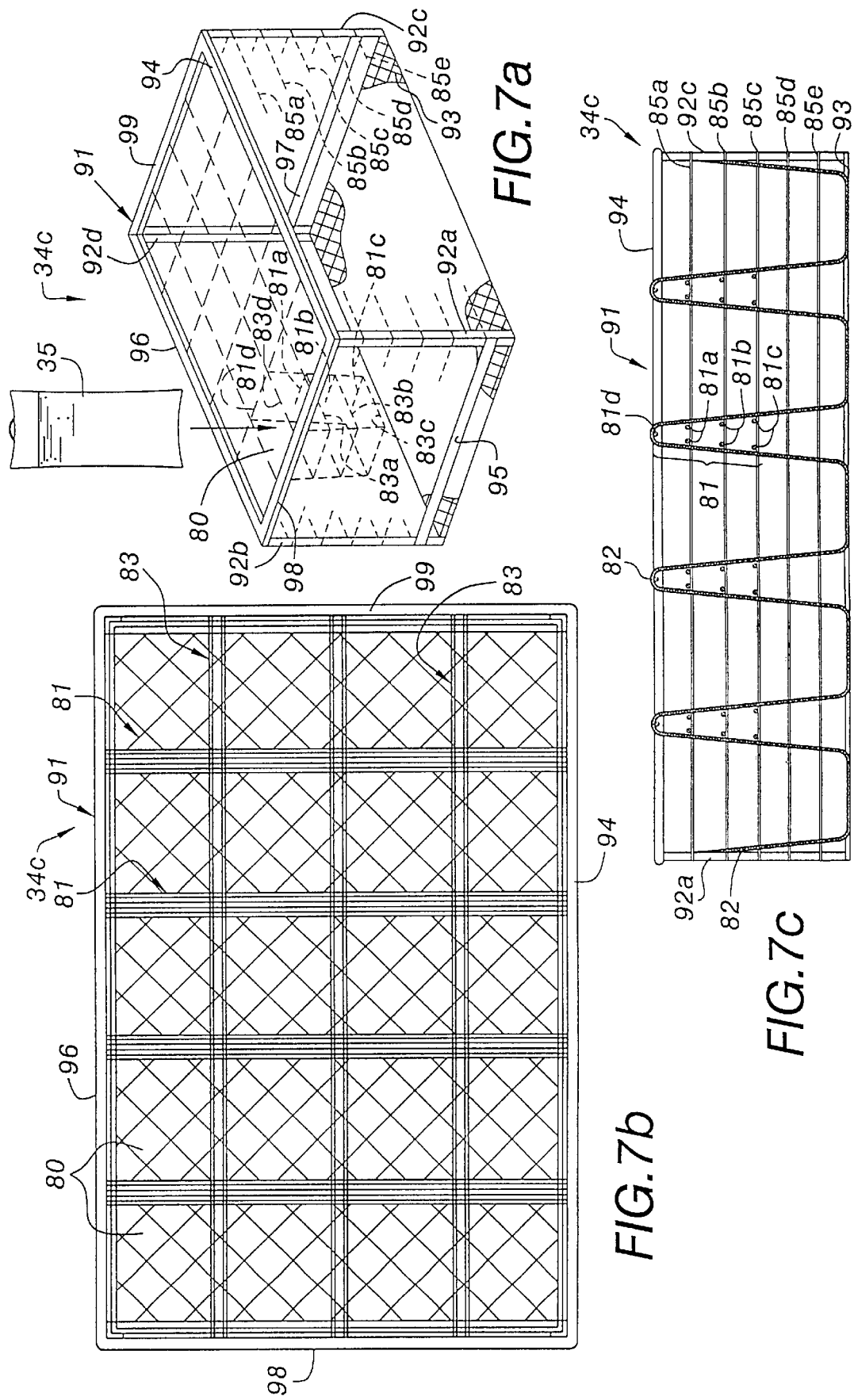

WARMING SYSTEM AND METHOD FOR HEATING VARIOUS ITEMS UTILIZED IN SURGICAL PROCEDURES

CROSS-REFERENCE TO RELATED APPLICATIONS

This application is a continuation-in-part of International Application No. PCT/US98/06951, entitled "Warming System and Method for Heating Various Items Utilized in Surgical Procedures", filed Apr. 7, 1998, which claims priority from U.S. Provisional patent application Ser. No. 60/042,737, entitled "Warmer Cabinet for Use in Surgical Procedures", filed Apr. 7, 1997. The disclosures of the above-mentioned International and provisional patent applications are incorporated herein by reference in their entireties.

BACKGROUND OF THE INVENTION

1. Technical Field

The present invention pertains to surgical warming systems for heating various items. In particular, the present invention pertains to a warming system and method for heating intravenous (IV) solution contained within bags and/or bottles, surgical instruments, blood and drugs placed within appropriate containers, or other objects for use in surgical procedures.

2. Discussion of Related Art

Generally, various items are required to be heated prior to utilization in a medical procedure to prevent thermal shock and injury to a patient. These items typically include intravenous solution, surgical instruments, bottles and blankets. In order to provide the necessary heated items for use in medical procedures, medical personnel may utilize several types of warming systems to heat items toward their operational temperatures. For example, ovens may be disposed within operating rooms to heat items to desired temperatures. Further, U.S. Pat. No. 4,495,402 (Burdick et al) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottommost article. Control circuitry is disposed beneath the plate to control the heater to maintain temperature of the bottommost article at a desired level based on the temperatures sensed by the first thermal sensor and a second thermal sensor responsive to heater temperature.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor enables automatic temperature regulation of the pad of heating filaments to heat the intravenous fluid bags. The heating filaments are covered by a rubber layer to prevent melting of the bags during heating. A temperature indicator disposed on the cabinet structure permits a user to ascertain when a desired temperature is attained, whereby an intravenous fluid bag is removed from the intravenous fluid warmer via an opening defined in a side of the cabinet structure.

The warming systems described above suffer from several disadvantages. In particular, ovens typically do not have a high degree of accuracy or control, thereby enabling use of items having temperatures incompatible with a medical procedure and possibly causing injury to a patient. Further, the Burdick et al and Bishop warmers employ heaters that generally contact a portion of the article being heated, thereby heating the articles in an uneven manner and enabling formation of hot spots. Moreover, the Burdick et al and Bishop warmers generally permit direct contact between an article and a heater, thereby enabling the article to become damaged from excess heat.

In order to overcome the aforementioned problems, some warming systems utilize heated air to heat articles placed within these systems. For example, U.S. Pat. No. 5,282,264 (Reeves et al) discloses an apparatus for thawing and warming solutions or fluids for intravenous administration. The solutions are typically contained within bags and placed within a tray disposed toward the top of an apparatus cabinet. A heating element is disposed within the apparatus cabinet whereby an impeller forces air past the heating element and into an air plenum. The air plenum extends from within the apparatus cabinet and curves over the top of the tray to direct and evenly distribute the heated air over various articles placed in the tray. A temperature sensor measures air temperature to enable a controller to maintain the heated air within a desired temperature range.

U.S. Pat. No. 5,297,234 (Harms et al) discloses an apparatus for rapid thermal processing of transfusion fluid, such as blood or blood components. The apparatus thaws a bag containing frozen blood or blood components by directing a flow of air across a heating coil. Temperature sensors measure the temperatures of the air and blood, whereby a control system monitors the sensed temperatures to maintain air temperature at a particular level, and to terminate thawing in response to a bag temperature of 30° C. The apparatus further enables rapid freezing of blood by directing air across a cooling coil and upon a bag containing blood to freeze that blood. The control system monitors sensed blood temperature via the temperature sensor, and terminates freezing in response to a bag or blood temperature of −30° C.

The warming systems described above utilizing heated air to warm items suffer from several disadvantages. In particular, the warming systems heat items simultaneously to only a single desired temperature, thereby being incompatible for applications requiring various items to be heated to different temperature ranges. Further, the warming systems control item temperature based on temperature of flowing air measured within a compartment separate from the items, thereby providing less accurate temperature control of the item storage compartment and for maintaining items at a desired temperature. Moreover, the warming systems have fixed storage capacities and are limited to a certain quantity or size of items, thereby being incompatible with items having dimensions beyond those of the respective system storage capacities, and/or requiring use of additional systems or heating cycles to accommodate additional items. Conversely, the warmer systems may utilize excess resources when used for quantities of items substantially less than their storage capacities. Therefore, there exists a need in the art for a surgical warming mechanism including multiple units or compartments under individualized control for simultaneously, accurately and independently maintaining the units or compartments at different desired temperatures in order to accommodate and maintain various quantities of items contained within the respective compartments at those different temperatures. In addition, there exists a need in the art for a surgical warming mechanism having an adjustable storage capacity to accommodate appropriate quantifies or sizes of items for particular applications.

OBJECTS AND SUMMARY OF THE INVENTION

Accordingly, it is an object of the present invention to simultaneously maintain various items at different desired temperatures for use in medical procedures.

It is another object of the present invention is to simultaneously maintain various items at different desired temperatures for use in medical procedures via a warming system constructed of individually controlled and various sized warmer units, whereby each warmer unit is maintained at an associated desired temperature.

Yet another object of the present invention to simultaneously maintain various items at different desired temperatures for use in medical procedures via a warming system including a single cabinet structure having multiple compartments, whereby each compartment is maintained at an associated desired temperature.

Still another object of the present invention is to simultaneously maintain various items at desired temperatures via a warming system having a selectively adjustable storage capacity to accommodate varying quantifies or sizes of items for different applications.

The aforesaid objects may be achieved individually and in combination, and it is not intended that the present invention be construed as requiring two or more of the objects to be combined unless expressly required by the claims attached hereto.

According to the present invention, a surgical warming system provides a manner in which to heat various medical items, primarily medical solutions generally contained within different sized bags and/or bottles, independently and simultaneously to enable the items to be immediately utilized for a particular medical application. The term "medical solutions" used herein refers to intravenous solutions, blood or other solutions that are administered intravenously to a patient. Specifically, the surgical warming system includes various compartments, at least one and generally two or more compartments, whereby each compartment is separately heatable and controllable over its own range of temperatures, typically in the approximate range of 86° F.–104° F. The compartments may be modular in the sense that the compartments may be implemented as separate warmer units that are stacked one atop the other. Alternatively, the multiple compartments may be constructed into a single cabinet structure whereby the compartments have varying dimensions, preferably to receive different sized intravenous bags and/or bottles. The heat within each compartment is provided by forcing air through a heating chamber and into the compartment whereby the forced air is recycled and mixed with make-up (e.g., outside) air to maximize control of air temperature. Each individually controllable compartment includes a corresponding heating unit and controller that enables an operator to simultaneously maintain the individual compartments of the same warming system at different desired temperatures in order to heat items or groups of items contained within the respective compartments to those different temperatures.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 1 is a view in perspective of an exemplary modular warmer unit according to the present invention.

FIG. 2 is a view in elevation of a rear panel of the warmer unit of FIG. 1 according to the present invention.

FIG. 6a is a top view in plan of a tray or drawer for disposing items within a warming system compartment to heat the items to a desired temperature according to the present invention.

FIG. 6b is a side view in elevation and partial section of the tray or drawer of FIG. 6a.

FIG. 6c is an exploded view in elevation and partial section of an alternative embodiment of the tray or drawer of FIGS. 6a–6b having an interchangeable bin.

FIG. 7a is a view in perspective of another embodiment of the tray or drawer of FIGS. 6a–6b having a configuration to enable storage of numerous medical solution containers in a generally upright position.

FIG. 7b is a top view in plan of the tray or drawer of FIG. 7a.

FIG. 7c is a front view in elevation and partial section of the tray or drawer of FIG. 7a.

FIG. 7d is a side view in elevation of the tray or drawer of FIG. 7a.

DETAILED DESCRIPTION OF THE PREFERRED EMBODIMENTS

Figure 3:
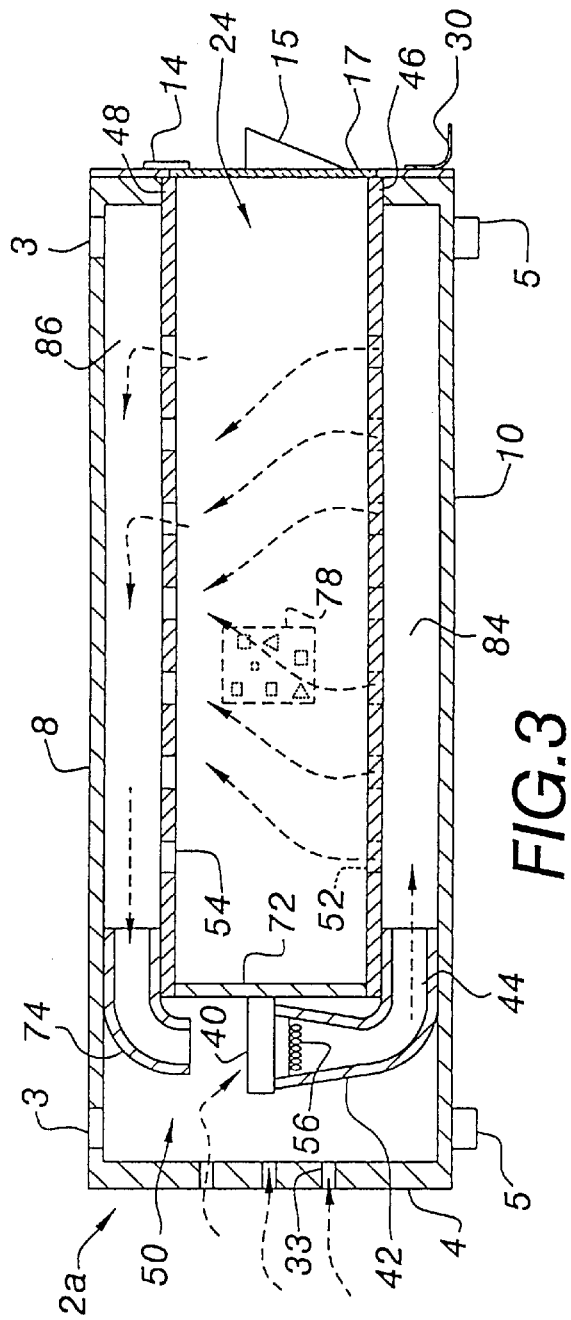
FIG. 3 is a side view in elevation and partial section of the warmer unit of FIG. 1 diagrammatically illustrating air flow paths through the warmer unit according to the present invention.

An exemplary surgical warmer unit 2a is illustrated in FIG. 1. Specifically, warmer unit 2a includes a rear panel 4, two substantially similar side panels 6, a top panel 8, a bottom panel 10 and a front panel 12. The top, side, front, rear and bottom panels are each substantially rectangular and define a cabinet interior wherein various medical or other items may be heated. The terms "top", "bottom", "side", "left", "right", "front", "rear", "upper", "lower", "length", "width", "height", "depth", "horizontal" and "vertical" are utilized herein merely to indicate points of reference and do not limit the present invention to any specific orientation or configuration. Warmer unit 2a includes a compartment 24 that is controlled by a corresponding process controller 16 (FIG. 8) to maintain a desired heating (i.e., temperature) range, whereby the compartment may be set and maintained at a desired temperature as described below. A series of substantially rectangular slots 3 are disposed toward the corners of top panel 8, while a plurality of substantially rectangular feet or tabs 5 extend from the proximity of the corners of bottom panel 10. Slots 3 include dimensions slightly larger than feet 5 to enable feet 5 of warmer unit 2a to be inserted within slots 3 of a warmer unit disposed below warmer unit 2a. This enables warmer units to be arranged in stack relation to form warming systems or cabinets having a plurality of warmer units (e.g., FIG. 9). The warmer unit slots and feet may be of any quantity, shape or size, and may be disposed on the warmer unit in any fashion.

Figure 8:
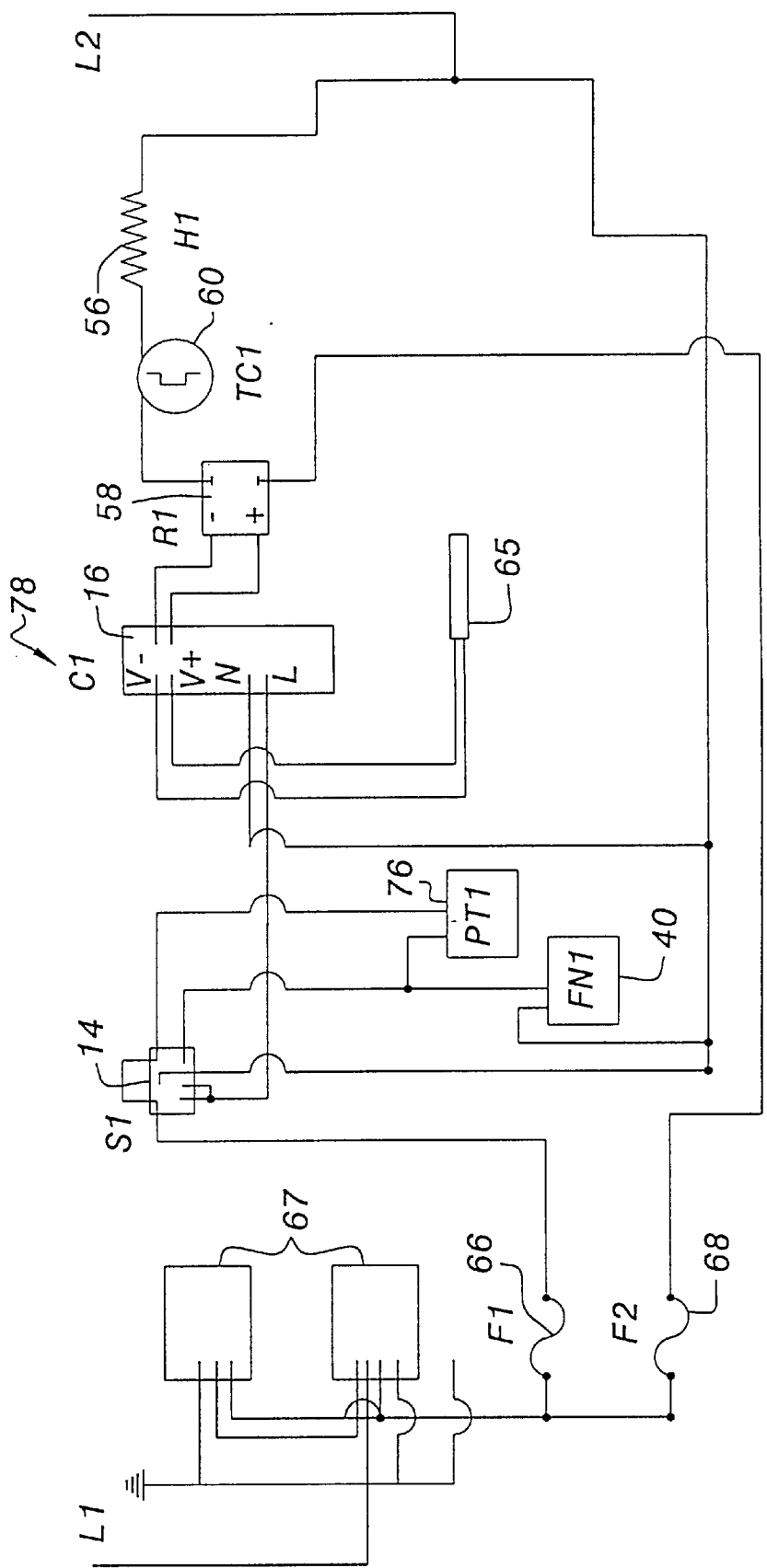
FIG. 8 is an electrical schematic diagram of an exemplary control circuit for the warmer unit of FIG. 1 according to the present invention.

Front panel 12 includes a power switch 14 and a temperature controller holder 15 typically disposed toward the upper portion of a front panel edge (e.g., the upper portion of a front panel rightmost edge as viewed in FIG. 1). Holder 15 is a pocket of substantially triangular cross-section with an open top portion to receive controller 16 (FIG. 8). The power switch and holder (e.g., along with the controller) may alternatively be disposed on the warmer unit in any fashion capable of operating the warmer unit. Power switch 14 enables power to controller 16 and a fan disposed within the warmer unit described below to commence heating the compartment to a desired temperature. Controller 16 is typically implemented by a microprocessor that displays a current temperature of the compartment and enables an operator to set a desired temperature for that compartment. Top panel 8 may further include an intravenous support or pole (not shown) to accommodate intravenous (IV) and/or irrigation fluid bags heated by warmer unit 2a for application to patients. The intravenous pole mounted on the warmer unit enhances efficiency by enabling immediate use of the warmed fluid since the pole and warmer unit are in close proximity. Moreover, top panel 8 may include a lamp or other light source (not shown) that illuminates the top panel such that an operator has sufficient light to transcribe information during a medical procedure. In addition, other items, typically utilized in an operating room, may be attached to warmer unit 2a to reduce consumption of operating room space.

Front panel 12 further includes a door 18 that enables access to compartment 24. Door 18 is substantially rectangular and is generally disposed within front panel 12 between power switch 14 and a front panel side edge (e.g., the leftmost side edge as viewed in FIG. 1). A substantially rectangular window 17, typically constructed of clear polycarbonate or other transparent material, is disposed on the door and includes dimensions slightly less than the door dimensions. Door 18 may vary in size according to the size of the warmer unit, and generally includes dimensions slightly less than front panel 12. The door is preferably connected to front panel 12 via hinges (not shown) disposed toward the door upper edges that enables the door to pivot upwards toward top panel 10. Further, door 18 includes a handle 30 disposed below window 17 and extending along a window bottom edge. Handle 30 is preferably implemented by an L-shaped handle that extends outward from an external surface of the door to enable an operator's hand to grip the handle and manipulate that door. Alternatively, handle 30 may be implemented by any handle capable of manipulating the door. Door 18 is typically manipulated to an open position to enable a warmer unit tray or drawer described below to access the compartment, whereby the drawer contains medical items to be heated by the warmer unit. The surgical warmer unit components (e.g., panels, walls, plates, doors, etc.) are typically constructed of a suitably sturdy or rigid material, such as aluminum, but may be implemented by any material (e.g., metals, plastics, etc.) capable of accommodating the desired component function described herein.

The warmer unit rear panel is illustrated, by way of example only, in FIG. 2. Specifically, rear panel 4 is substantially rectangular as described above and includes dimensions substantially similar to front panel 12 (FIG. 1). A plurality of slots 33 is defined in the rear panel to permit air to enter the warmer unit to be heated for maintaining compartment temperature as described below. Slots 33 are generally elliptical slots having their major axes extending along the longer dimension of rear panel 4, whereby the major axes of the slots are substantially greater than the slot minor axes. Slots 33 are generally defined in rear panel 4 in groups of three rows (e.g., each row extends across the longer dimension of the rear panel) with each row having two adjacent slots, whereby a group of slots is disposed coincident compartment 24. However, rear panel 4 may include any quantity (e.g., at least one) of slots whereby the slots may be of any shape or size and may be arranged in any fashion capable of enabling air to enter the warmer unit.

Referring to FIG. 3, compartment 24 includes side walls 70, a rear wall 72 and respective floor and ceiling plates 46 and 48. The compartment side and rear walls 70, 72 and floor and ceiling plates 46 and 48, respectively, are substantially rectangular wherein side walls 70 extend from front panel 12 toward rear panel 4, and from bottom panel 10 to top panel 8. Side and rear walls 70, 72 of compartment 24 are disposed about the peripheral edges of floor and ceiling plates 46 and 48 with rear wall 72 disposed between the floor and ceiling plates. The side and rear walls and the floor and ceiling plates collectively define a compartment interior wherein medical or other items may be heated. Floor and ceiling plates 46 and 48 have substantially similar dimensions and include holes defined in the respective floor and ceiling plates to permit air flow through the compartment as described below.

Figure 9:
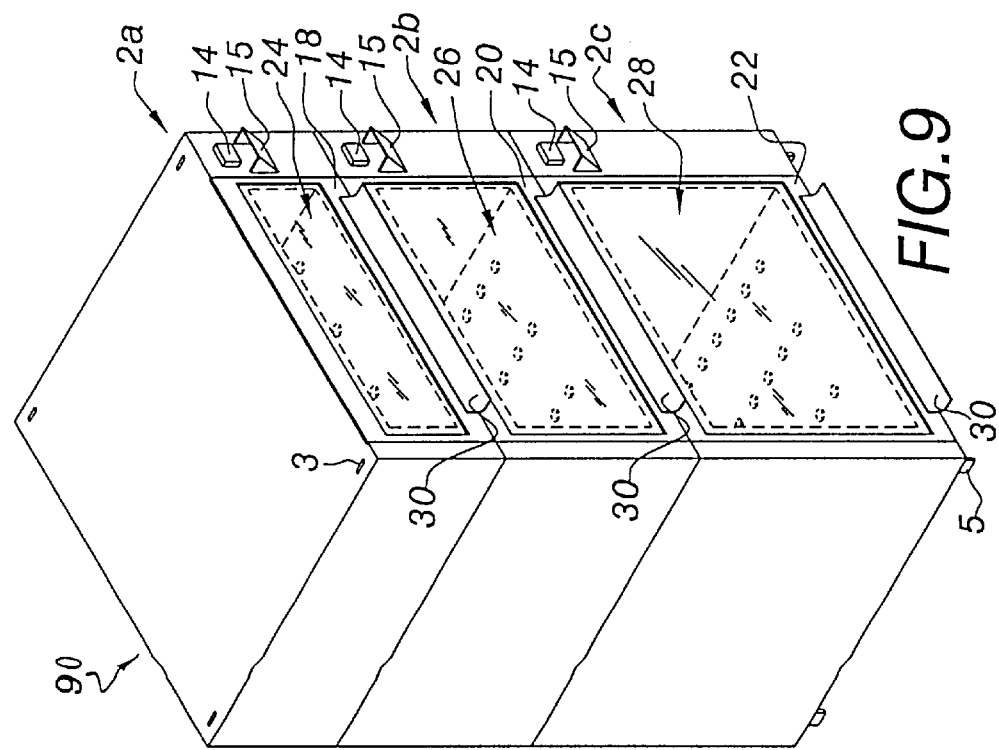
FIG. 9 is a view in perspective of a warming system including a plurality of warmer units of the type of FIG. 1 to simultaneously maintain various objects at different desired temperatures according to the present invention.

Compartment 24 is essentially in the form of a rectangular box wherein length and width dimensions of the compartment are similar, however, the length (e.g., compartment depth) and width (e.g., compartment height) of side and rear walls 70, 72, may vary to produce compartments of different sizes or capacities (e.g., FIG. 9). The length and width dimensions of compartment 24 are slightly less than the warmer unit interior length and width dimensions such that a short distance resides between side walls 70 and side panels 6, and between rear wall 72 and rear panel 4. In addition, a slight distance resides between compartment 24 and bottom panel 10, and between compartment 24 and top panel 8. The distances between the compartment and the top and bottom panels form lower and upper cavities 84, 86, respectively, that enable air flow through the compartment as described below. The lower and upper cavities are substantially rectangular and have dimensions substantially similar to respective floor and ceiling plates 46 and 48. The distance between compartment rear wall 72 and rear panel 4 serves as an air chamber 50 whereby outside air enters warmer unit 2a via slots 33 defined in the warmer unit rear panel as described above.

A heater in the form of a conventional fan 40 with a corresponding heating coil 56 is mounted on an exterior surface of rear wall 72 of compartment 24 and forces air from air chamber 50 and upper cavity 86 over the heating coil to produce heated air that heats items disposed within the compartment. Air from upper cavity 86 is received by fan 40 via an upper manifold 74 disposed proximate the upper cavity and extending toward the fan. The heated air flows through compartment 24 as described below whereby the heated air is recycled (e.g., re-used within that compartment) and mixed with outside air in various concentrations, depending upon the current compartment and desired temperatures, to control the compartment temperature. Compartment 24 further includes a thermocouple 65 (FIG. 8), typically implemented by a conventional or other type of temperature sensor, that measures the temperature within the compartment and sends a temperature signal to the controller as described below. The thermocouple is typically disposed within compartment 24 in one of the compartment side walls 70 at a height corresponding to approximately a middle height of the compartment.

Warmer unit 2a heats a mixture of outside or make-up air and recycled air (e.g., air previously utilized within the particular compartments) and forces the heated air to flow proximate a tray or drawer disposed within compartment 24 in order to heat the medical items contained within the drawer to a desired temperature. Fan 40 is disposed on an exterior surface of compartment rear wall 72 toward the uppermost portion of the compartment. Fan 40 draws air into the compartment from upper cavity 86 (e.g., via upper manifold 74) and air chamber 50, whereby air infiltrates the air chamber via rear panel slots 33 as described above. A duct 42 is disposed beneath fan 40 and receives air driven by the fan. Duct 42 is substantially trapezoidal (e.g., the duct include a substantially trapezoidal cross-section) and extends from fan 40 toward lower cavity 84. The width of the duct gradually narrows from fan 40 toward the lower cavity whereby the duct is similar in configuration to a funnel.

Figure 4:
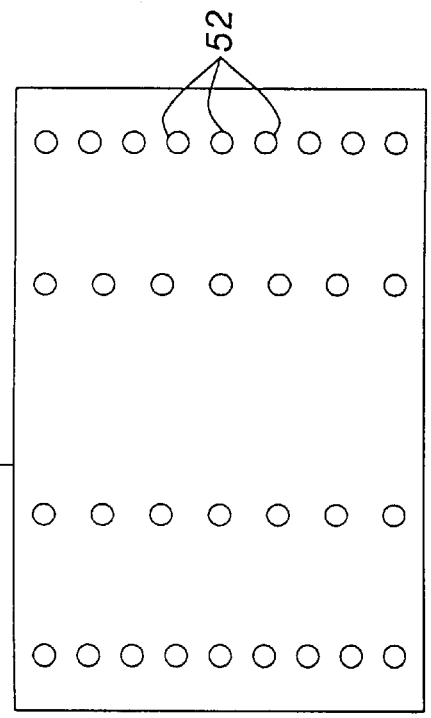
FIG. 4 is a top view in plan of a warming system compartment floor plate for directing heated air flow to enter a warming system compartment according to the present invention.

Duct 42 includes heating coil 56 disposed within the duct toward fan 40 to heat the air. The duct directs or funnels air over heating coil 56 and through a lower manifold 44 disposed at a distal end of the duct. The lower manifold directs the air through lower cavity 84 and into the compartment via floor plate 46 that is disposed above the lower cavity. Referring to FIG. 4, floor plate 46 is substantially rectangular having length and width dimensions substantially similar to the compartment length and width dimensions whereby the floor plate includes a plurality of holes or apertures 52 defined within the floor plate. Holes 52 are typically arranged through floor plate 46 in four columns (e.g., as viewed in FIG. 4 with each column extending in a direction of the floor plate shorter dimension edges or floor plate transverse axis from the front to the rear of the compartment) with each column spaced a sufficient distance to encompass the floor plate surface whereby the hole columns disposed toward the floor plate shorter dimension edges each generally include a greater quantity of holes than the remaining columns. The holes enable heated air from lower cavity 84 (FIG. 3) to enter the compartment.

Figure 5:
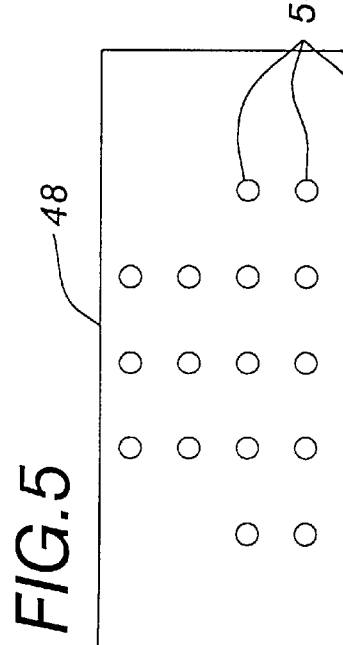
FIG. 5 is a top view in plan of a warming system compartment ceiling plate for directing heated air flow to exit a warming system compartment according to the present invention.

The heated air traverses compartment 24 and the drawer containing medical items to heat those items, and exits the compartment via ceiling plate 48 illustrated in FIG. 5. Specifically, ceiling plate 48 is substantially similar to floor plate 46 (FIG. 4) except that the ceiling plate includes a plurality of holes or apertures 54 defined within the ceiling plate in a different arrangement. Holes 54 are typically arranged through ceiling plate 48 in five columns (e.g., as viewed in FIG. 5 with each column extending in the direction of the ceiling plate shorter dimension edges or ceiling plate transverse axis from the front to the rear of the compartment) substantially evenly spaced and concentrated about the ceiling plate center whereby the hole columns disposed toward the ceiling plate shorter dimension edges each generally include a lesser quantity of holes than the remaining columns. Holes 54 defined in ceiling plate 48 enable heated air to exit the compartment into upper cavity 86 (FIG. 3). The ceiling plate typically includes a substantially lesser amount of holes than floor plate 46.

The particular arrangements of the holes within the floor and ceiling plates create a flume-like effect within the compartment to direct heated air toward the middle of the compartment. In other words, the heated air enters the compartment and is directed inwardly toward the middle of the compartment to prevent the heated air from flowing around the outside of the medical items contained within the drawer (e.g., to prevent greater heating around the edges by concentrating more of the air flow onto the drawer). The flume-like air flow within the compartment enables the air to efficiently and evenly heat the items contained within the compartment drawer. Air flow from the ceiling plate is received in the upper cavity disposed above the ceiling plate, whereby the air enters the upper manifold that directs the heated air back into the fan within the air chamber.

Medical items are disposed within compartment 24 whereby heated air flow is distributed substantially evenly about items within the compartment to heat those items evenly to a desired temperature. A tray or drawer 34a for utilization within compartment 24 to heat various medical items is illustrated in FIGS. 6a–6b. Specifically, drawer 34a includes a plurality of bins 36 for receiving medical items to be heated within the warmer unit compartment. Bins 36 are disposed adjacent each other whereby each bin includes a mesh or wire container for receiving the medical items and enabling free flow of heated air through the bins to heat the medical items to a desired temperature. The drawer size varies in accordance with dimensions of compartment 24 and may include any number of bins 36. Alternatively, multiple drawers may be utilized within a single compartment that includes sufficient storage capacity to accommodate the drawers.

Drawer 34a includes a substantially rectangular frame 88 having length and width dimensions slightly less than the length and width dimensions of the compartment. A series of transversely spaced rods or bars 38 extend across a shorter dimension of drawer frame 88 to enable mesh or wire to attach to the frame and rods to form individual bins 36 between the rods. The drawer frame and rods may be constructed of any suitably sturdy or rigid material that can withstand the compartment temperature, while the mesh may be implemented by wire, rope or other material that enables air flow through the drawer and can withstand the compartment temperature. Alternatively, drawer 34a may include a series of adjacent bins formed of plastic or other suitable material having multiple holes defined therein to enable the heated air to infiltrate the bins and heat the items contained within the drawer.

Drawer 34a is typically disposed on runners or tracks (not shown) mounted on an interior surface of side walls 70 (FIG. 1) of compartment 24 that enable the drawer to smoothly slide into and out of the compartment. This sliding mechanism is similar to that used in drawers within common desks. The drawer may further be removed from the runners or tracks and be replaced by another drawer of a different configuration for handling other types or sizes of medical items as described below. Door 18 is typically manipulated to an open position to enable access to drawer 34a within compartment 24.

Drawer 34a may further include various configurations to contain medical items for heating within compartment 24. For example, the drawer bins may be interchangeable to accommodate various types or sizes of medical items as illustrated in FIG. 6c. Specifically, drawer 34b is substantially similar to drawer 34a described above, except that each bin may be removably secured to the drawer frame and replaced by another bin having a different configuration to heat various medical items. In particular, an interchangeable bin 37 includes a substantially rectangular bin frame 39 having dimensions compatible with a corresponding bin space defined by rods 38 and frame 88. Mesh or wire is attached to bin frame 39 to form a container within the interchangeable bin for containing medical items. The bin frame may be constructed of any suitably sturdy or rigid material that can withstand the compartment temperature, while the mesh may be implemented by wire, rope or other material that enables air flow through bin 37 and can withstand the compartment temperature. Alternatively, bin 37 may be formed by plastic or other suitable material attached to the bin frame and having holes defined therein to enable heated air to infiltrate the bin and heat the medical items contained therein.

Bin fasteners 41 are typically disposed on the underside of the bin frame, while corresponding drawer fasteners 43 are generally disposed on rods 38 and frame 88 to engage bin fasteners 41 and removably attach bin 37 to the drawer. Fasteners 41, 43 may be implemented by any conventional or other types of fasteners, such as ties, hooks, snaps, clasps, velcro, etc., and may be disposed in any quantity or combination and at any suitable locations on the bin and/or drawer. Bin 37 is typically removed from drawer 34b and replaced, via fasteners 41, 43, with a new bin having a different configuration to accommodate medical items of various types or sizes. For example, bin 37 having a configuration to contain medical solution containers may be replaced with a bin of greater storage capacity or a specific configuration for heating other medical items, such as blankets or instruments. It is to be understood that the drawer may include any quantity or combination of fixed and/or interchangeable bins of any shape or size.

In addition, an entire drawer may be interchanged with another drawer having a different bin configuration (e.g., quantity of bins, bin storage capacity, interchangeable bins, etc.) to accommodate various medical items. For example, a drawer having bins configured to contain medical solution containers may be replaced by a drawer having a bin configuration suitable for containing instruments, or a bin configuration suitable for containing blankets. A drawer may be removed from the warmer unit compartment as described above and replaced with a new drawer for use with the unit. Thus, the warmer unit and drawer may serve various functions depending upon the particular drawer or bin configurations utilized by that unit.

Another embodiment of the tray or drawer for accommodating numerous medical solution containers in a generally upright position is illustrated in FIGS. 7a–7d. Specifically, drawer 34c includes a generally box-like configuration having an upper frame 91 and a floor 93. Upper frame 91 and floor 93 are each substantially rectangular and have substantially similar dimensions. The upper frame includes front and rear bars 94, 96 and side bars 98, 99, each substantially rectangular and collectively defining a generally open upper frame interior to enable placement of items within the drawer. Floor 93 is aligned substantially coincident with upper frame 91 and includes a mesh interior, preferably formed of wire mesh. Posts 92a–92d are each disposed toward a corresponding drawer corner to interconnect the frame to the floor. A support bar 95 extends along the shorter dimension edge of the floor and is attached to corresponding posts 92a, 92b. Similarly, a support bar 97 is disposed along the opposing shorter dimension edge of the floor and is attached to corresponding posts 92c, 92d. The support bars are each substantially rectangular and extend between the respective posts at a slight distance above floor 93 to structurally strengthen the drawer.

The drawer interior is partitioned into a plurality of receptacles 80, each for containing a medical solution container 35, such as an intravenous (IV) solution bag. Mesh material (FIG. 7b) is attached to upper frame 91 and disposed within each receptacle to contain items as described below. The receptacles typically have sufficient storage capacity to accommodate container 35 in a generally upright position. In this fashion, drawer 34c may contain numerous medical solution containers or other medical items within compartment 24 for heating to a desired temperature.

In order to form receptacles 80, drawer 34c includes a plurality of dividers that partition the drawer interior. In particular, drawer 34c includes transverse dividers 81 and longitudinal dividers 83. Transverse dividers 81 extend substantially in parallel between front and rear upper frame bars 94, 96, and are spaced apart along the upper frame longer dimension. Longitudinal dividers 83 extend substantially in parallel between upper frame side bars 98, 99 and are spaced apart along the upper frame shorter dimension. The transverse and longitudinal dividers are generally orthogonal to each other and essentially form a grid to partition the drawer interior into individual receptacles 80.

Transverse dividers 81 each include a series of wire members 81a–81d (FIG. 7c). Wire member 81d includes a single wire attached to and extending between front and rear upper frame bars 94, 96. Wire members 81a–81c each include a pair of horizontal wires extending substantially in parallel between front and rear upper frame bars 94, 96. Wire 81d forms the intersection of two planes tilted slightly from vertical, each plane including a respective wire from each of the wire pairs 81a–81c. The wires in each plane are spaced generally vertically and are oriented parallel to one another. The distance between wires in each wire pair 81a–81c successively increases as the wire pair position is further away from upper frame 91 and closer to floor 93. A series of peripheral wire members 85a–85e extend about the drawer periphery and are vertically spaced apart between the upper frame and floor. Wire members 81a–81c of each transverse divider 81 are vertically positioned between the upper frame and floor at locations corresponding to the vertical positions of respective peripheral wire members 85a–85c.

A support wire member 82 extends along the drawer longer dimension between posts 92a, 92c and generally on the exterior side of the peripheral wire members, and has each end attached to a corresponding post. The support wire member repeatedly extends between the upper frame and floor in a generally wave-like pattern. In particular, the support wire member extends over each divider 81 and along floor 93 between dividers 81, between a divider 81 and post 92a and between a divider 81 and post 92c. The increased spacing between wire pair members of wire members 81a–81c and the single wire of wire member 81d provide the support wire member pattern with rounded peaks and substantially trapezoidal valleys. Support wire member 82 is attached to upper frame 91 and floor 93 proximate the peaks and valleys, respectively. Another wire member (not shown) is attached to and disposed in substantially the same manner between posts 92b, 92d along the drawer rear portion. Wire members 81a–81d of each transverse divider are connected to the support wire members at locations within the interior sections of the peaks that extend over the transverse dividers.

Figure 7D:
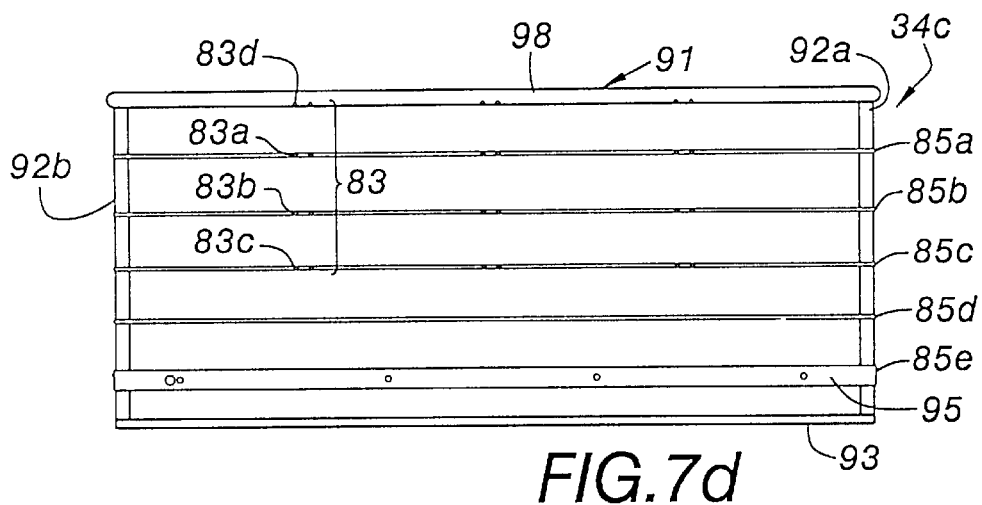

Longitudinal dividers 83 each include a series of wire members 83a–83d (FIG. 7d). Wire member 83d includes a pair of wires attached to and extending substantially in parallel between side bars 98, 99. Wire members 83a–83c similarly include a pair of horizontal wires extending substantially in parallel between bars 98, 99. Wire members 83a–83d are essentially contained within two parallel planes, each plane including a respective wire from each of the wire pairs 83a–83d. The wires in each plane are spaced generally vertically and are oriented parallel to one another. The members of each wire pair are separated by substantially the same distance. Wire members 83a–83c of each longitudinal divider have their ends attached to corresponding peripheral wire members 85a–85c between respective posts 92a, 92b and 92c, 92d. The wire members are vertically positioned between the upper frame and floor at locations corresponding to the vertical positions of respective peripheral wire members 85a–85c.

The longitudinal divider wire members may extend over or under the transverse divider wire members within the drawer interior to partition the drawer interior into receptacles 80, each having sufficient storage capacity to contain medical solution container 35 in a generally upright position. Mesh material is attached to the longitudinal and transverse dividers and/or upper frame to form containers for the individual receptacles for containing medical items. The mesh material and floor enable heated air from the compartment to infiltrate the receptacles and heat the items contained therein. The upper frame, floor, posts and support bars may be of any size or shape and may be constructed of any suitably sturdy or rigid material that can withstand the compartment temperature. In addition, the mesh material may be implemented by wire, rope or other material that enables air flow through the receptacles and can withstand the compartment temperature, while the wire members of the dividers may be implemented by any wire, rope, cable, string or other line of any size or cross-sectional shape that can withstand the compartment temperature.

Drawer 34c may include any quantity of interchangeable receptacles that may be replaced with receptacles or groups of receptacles having different configurations for containing medical items of different types or sizes. The receptacles may each include a receptacle frame with the receptacle frame and/or transverse and longitudinal dividers including fasteners to removably secure the receptacles to the drawer in substantially the same manner described above. In addition, drawer 34c may alternatively have a configuration that is adjustable to include several receptacles as described above or a single large receptacle for accommodating large medical items, such as blankets. The transverse and longitudinal dividers may be disposed in sliding relation with posts 92a–92d between the upper frame and floor. When the transverse and longitudinal dividers are positioned adjacent floor 93, the drawer contains a single large receptacle, while positioning of the transverse and longitudinal dividers toward upper frame 91 forms individual receptacles 80.

Figure 7E:
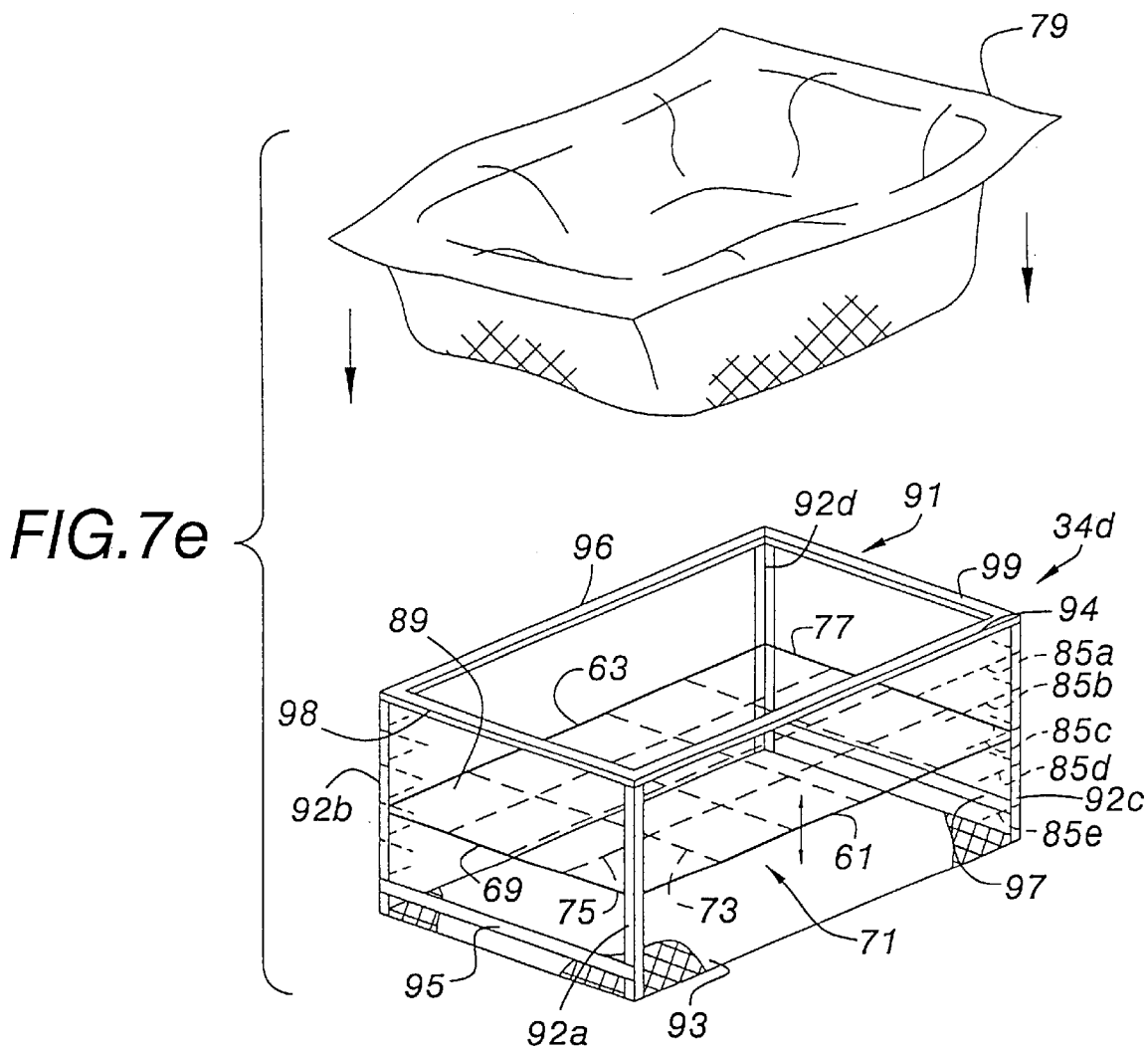
FIG. 7e is an exploded view in perspective of yet another embodiment of the tray or drawer of FIG. 7a having an adjustable configuration.

The adjustable configuration may be accomplished, for example, by a drawer having a partition frame mounted in slidable relation with posts 92a–92d between the upper frame and floor as illustrated in FIG. 7e. Drawer 34d is substantially similar to drawer 34c described above, except that drawer 34d includes an adjustable configuration. Specifically, drawer 34d includes a generally box-like configuration having an upper frame 91 and a floor 93 each as described above. The upper frame includes front and rear bars 94, 96 and side bars 98, 99. These bars are each substantially rectangular and collectively define a generally open upper frame interior to enable placement of medical items within the drawer. Floor 93 is aligned substantially coincident with frame 91 and includes a mesh interior, preferably formed of wire mesh. Posts 92a–92d are each disposed toward a corresponding drawer corner to interconnect the frame to the floor. Support bars 95, 97 are attached to and disposed between corresponding posts 92a, 92b and 92c, 92d slightly above the drawer floor to structurally strengthen the drawer as described above. In addition, peripheral wire members 85a–85e are disposed about the drawer periphery and are vertically spaced between the upper frame and floor as described above.

A partition frame 71 is disposed between upper frame 91 and floor 93. The partition frame is substantially rectangular and includes front and rear rods 61, 63 and side rods 69, 77. Partition frame 71 has dimensions substantially similar to upper frame 91 and floor 93, and further includes transverse dividers 73 and longitudinal dividers 75. The transverse dividers are attached to and extend substantially in parallel between front and rear rods 61, 63, while being spaced apart along the partition frame longer dimension. The longitudinal dividers are attached to and extend substantially in parallel between side rods 69, 77. The longitudinal dividers are spaced apart along the partition frame shorter dimension and are substantially orthogonal to the transverse dividers, thereby forming a grid pattern for defining several individual receptacles 89. The upper frame, floor, partition frame and dividers, posts and support bars may be of any size or shape and may be constructed of any suitably sturdy or rigid material that can withstand the compartment temperature.

The partition frame is supported within the drawer interior by tracks or slots (not shown) disposed on posts 92a–92d. The tracks or slots may include any conventional or other mechanisms to engage partition frame corners and enable the partition frame to slide relative to the posts and maintain a position between the upper frame and floor for adjusting the drawer configuration as described below. Mesh material 79 is attached to the upper frame to form a container within the drawer to contain medical items. The mesh material may be implemented by wire, rope or other material that enables air flow through the drawer and can withstand the compartment temperature.

When partition frame 71 is positioned adjacent floor 93, the drawer contains a single large receptacle for containing medical items, such as blankets. Conversely, the partition frame may be positioned toward upper frame 91, while mesh material 79 is inserted through the partition frame spaces defined by the transverse and longitudinal dividers, thereby defining containers for several individual receptacles 89. The position of the partition frame relative to the drawer floor determines the storage capacity of the receptacles and the size of the medical items that may be contained therein. For example, positioning frame 71 toward upper frame 91 enables the receptacles to contain a medical solution container, such as container 35, in a generally upright position as described above, while sliding the partition frame toward floor 93 provides storage capacity for smaller medical items. The partition frame may be located at any desired position between the upper frame and floor to accommodate various types or sizes of items.

Referring back to FIG. 3, the air flow path through compartment 24 is described with reference to the arrows indicating the air flow path. Specifically, outside air infiltrates warmer unit 2a via slots 33 defined in rear panel 4 and flows into air chamber 50 whereby the outside air mixes with heated air flowing from the compartment. Fan 40 directs air from chamber 50 and upper manifold 74 through duct 42 whereby heating coil 56 disposed in the air flow path within the duct heats the air. The heated air is then directed into lower cavity 84 via lower manifold 44 whereby the air traverses the floor plate into the compartment. The air flows within the compartment in a flume-like fashion described above through a drawer (e.g., any of drawers 34a–34d described above) to heat items contained within the drawer, and exits the compartment via ceiling plate 48 into corresponding upper cavity 86. Upper manifold 74 directs the air from upper cavity 86 back to fan 40 within air chamber 50 to mix with fresh or make-up air and be recirculated into the compartment as described above to heat the medical items. The mixture of recycled and fresh air distributed to the compartment via fan 40 is controlled in a conventional manner based on the compartment and desired temperatures in order to efficiently maintain the compartment at the desired temperature.

A control circuit 78 for controlling the warmer unit compartment to heat medical items is illustrated in FIG. 8. Specifically, control circuit 78 is typically mounted on a warmer unit side panel in the space between that side panel and a corresponding side wall of the warmer unit compartment. Control circuit 78 includes power switch 14 connected in series with compartment fan 40, a purge timer 76 and temperature controller 16. Switch 14 is operator controlled and enables activation of fan 40 and controller 16 whereby fan 40 may be implemented by conventional blowers or fans that direct air over heating coil 56 and through the compartment as described above. Purge timer 76 enables activation of fan 40 for approximately three to five minutes subsequent to switch 14 disabling operation of the warmer unit to dissipate heat from and cool heating coil 56 in order to prevent damage to the warmer unit from excessive heat.

Temperature controller 16 is typically implemented by a microprocessor controller, for example, model 2132 proportional-integral-derivative (PID) controller manufactured by Eurotherm Controls, Ltd. of England. Controller 16 typically includes a display and enables an operator to set a desired compartment temperature via manipulation of display buttons that modify control parameters (e.g., temperature, mode of operation etc.) of the controller. Further, the display of controller 16 provides the temperature of the compartment via signals received by thermocouple 65 disposed within that compartment described above. In other words, the controller is essentially a microprocessor, generally pre-programmed with its own software, that senses and controls compartment temperature in accordance with PID control.

Controller 16 is connected to thermocouple 65 and in series with a solid state relay 58 that receives logic signals from the controller to close that relay and enable operation of heating coil 56 in accordance with the difference between the selected and existing compartment temperatures. Controller 16 essentially utilizes PID control to adjust the current through heating coil 56 via relay 58 to maintain the compartment at a desired temperature based on the desired and current compartment temperatures. Heating coil 56 is disposed in series with solid state relay 58, and receives current from that relay to dissipate heat in order to heat the air within duct 42 (FIG. 3). High limit or overload switch 60 is connected between and in series with solid state relay 58 and heating coil 56, and enters an open state to disable the heating coil by shunting excess current from the heating coil when the current exceeds a threshold level (e.g., a level that may damage the warmer unit or circuit). Switch 14 and solid state relay 58 are connected in series with corresponding fuses 66, 68, respectively, to protect the circuit from excess current. Fuses 66, 68 are in turn connected in series with power receptacles 67. The receptacles typically receive power from a common wall outlet jack via a detachable power cord (not shown). The various control circuit components are typically implemented via conventional or commercially available components and/or may be implemented by any circuitry based on the functional description of the circuit described above.

Operation of the warmer unit is described with reference to FIGS. 1, 3 and 8. Specifically, various medical items, such as intravenous or irrigation fluids, blood, instruments or drugs, are selected to be placed within warmer unit 2a. Door 18 is manipulated to an open position whereby a drawer (e.g., any of drawers 34a–34d described above) may be retrieved from or inserted (e.g., if no drawer is present) into the compartment. Further, an entire drawer may be replaced with another drawer, or individual drawer bins or receptacles may be replaced by other bins or receptacles to accommodate various medical items as described above. The medical items are inserted into the drawer and the drawer is placed into the compartment with the compartment door subsequently manipulated to a closed position. Power switch 14 is actuated to enable operation of control circuit 78 and fan 40 to direct air over heating coil 56 and through the compartment as described above. Controller 16 is manipulated via display buttons to set that controller to maintain the compartment at a desired temperature, typically in the approximate range of 86° F.–104° F. The controller further displays the current compartment temperature as measured by thermocouple 65 disposed within the compartment. When the medical items have attained the desired temperature, the drawer is retrieved from the compartment and the items are removed from the drawer for use in a medical or other procedure.

An exemplary warming system including multiple warmer units is illustrated in FIG. 9. Specifically, warming system 90 includes warmer units 2a, 2b 2c arranged in stack relation. Warmer unit 2a is substantially similar to and functions in substantially the same manner as the warmer unit described above for FIG. 1. Similarly, warmer units 2b, 2c are substantially similar to and function in substantially the same manner as warmer unit 2a except that warmer units 2b, 2c include slightly greater dimensions to accommodate larger sized or greater quantities of items. For example, warmer unit 2b includes dimensions greater than warmer unit 2a, while warmer unit 2c includes dimensions greater than warmer unit 2b. Warmer units 2a, 2b, 2c include respective compartments 24, 26, 28, and are individually controlled to maintain those compartments at desired temperatures in substantially the same manner described above. The warmer units are typically vertically arranged, by way of example only, with warmer unit 2a disposed as the top unit, warmer unit 2c disposed as the bottom unit, and warmer unit 2b disposed between warmer units 2a, 2b. Feet 5 of each warmer unit is inserted within slots 3 of the warmer unit disposed adjacent and below that unit to securely arrange the warmer units in stack relation. Each warmer unit includes at least one appropriately sized drawer (e.g., any of drawers 34a–34d described above) to enable items to be placed and removed within the corresponding compartment as described above. Warming system 90 may include any quantity of any sized warmer units whereby the warmer units may be selectively added or removed to the warming system. Thus, the warming system storage capacity may be adjusted to accommodate various quantities or sizes of items for particular applications. In addition, any individual warmer unit or combination of warmer units within warming system 90 may be actuated to heat items depending upon the size or quantity of items required to be heated.

In operation, various medical items, such as intravenous or irrigation fluids, blood, instruments or drugs, are selected to be placed within warming system 90. An appropriate warmer unit 2a, 2b, 2c for receiving the items is selected based on the size of the items and the capacity of the warmer unit. A door 18, 20, 22 of the selected warmer unit is manipulated to an open position whereby a drawer (e.g., any of drawers 34a–34d described above) may be retrieved from or inserted (e.g., if no drawer is present) into that compartment. Further, an entire drawer may be replaced with another drawer, or individual drawer bins or receptacles may be replaced by other bins or receptacles to accommodate various medical items as described above. The medical items are inserted into the drawer and the drawer is placed into the selected warmer unit compartment with that compartment door subsequently manipulated to a closed position. A power switch 14 associated with the selected warmer unit is actuated to enable operation of a corresponding fan to direct air over a corresponding heating coil and through the compartment as described above. A corresponding controller (not shown) is manipulated via display buttons to set that controller to maintain the selected warmer unit compartment at a desired temperature, typically in the approximate range of 86° F.–104° F. The corresponding controller further displays the current compartment temperature of the selected warmer unit as measured by a thermocouple disposed within that compartment as described above. When the medical items have attained the desired temperature, the drawer is retrieved from the selected warmer unit and the items are removed from the drawer for use in a medical or other procedure. This process may be repeated for remaining warmer units within warming system 90 to simultaneously heat various items to different temperatures.

The surgical warmer unit or warming system described above may be utilized in conjunction with an intravenous (IV) warming apparatus, such as an apparatus that heats intravenous solution as the solution is delivered to the patient from an intravenous bag or other container. Initially, the temperature of intravenous solution contained within an intravenous bag is generally unknown, within thirty degrees Fahrenheit or more, when the bag is hung on an intravenous rack or pole. The surgical warmer unit or warming system permits pre-heating of an intravenous solution bag to a desired temperature such that, upon removal from the warmer unit or warming system, the bag may be placed into a heated intravenous warmer suspended proximate a patient. Further, the warmer unit or warming system may also be used in combination with a thermal treatment machine having a basin for heating solutions, such as the machine disclosed in U.S. Pat. No. 5,333,326 (Faries, Jr. et al), the disclosure of which is incorporated herein by reference in its entirety. In this instance, bags or bottles of various solutions, such as irrigation fluid, may be placed in the warmer unit or warming system to be heated to a desired temperature. The heated bag or bottle is removed from the warmer unit or warming system with the contained solution at the desired temperature, and the solution is placed in the basin for available use more quickly during a surgical procedure since the solution is already heated to a temperature near its operational temperature.

Generally, the surgical warmer unit or warming system is set to heat the intravenous or irrigation solutions to temperatures slightly below their end use or operating temperatures, thereby making it is easier for the intravenous warmer or basin to warm the solutions to their desired operating temperatures. The warmer unit or warming system warmer unit temperatures are typically set slightly below the solution operating temperature since it is easier to additionally warm the liquid in use within the intravenous warmer and thermal treatment machine rather than wait for the solutions to cool to the appropriate operating temperature. Thus, the intravenous or irrigation fluid heating time within the intravenous warmer and thermal treatment machine, respectively, is drastically reduced by use of the warmer unit or warming system.

Figure 10:
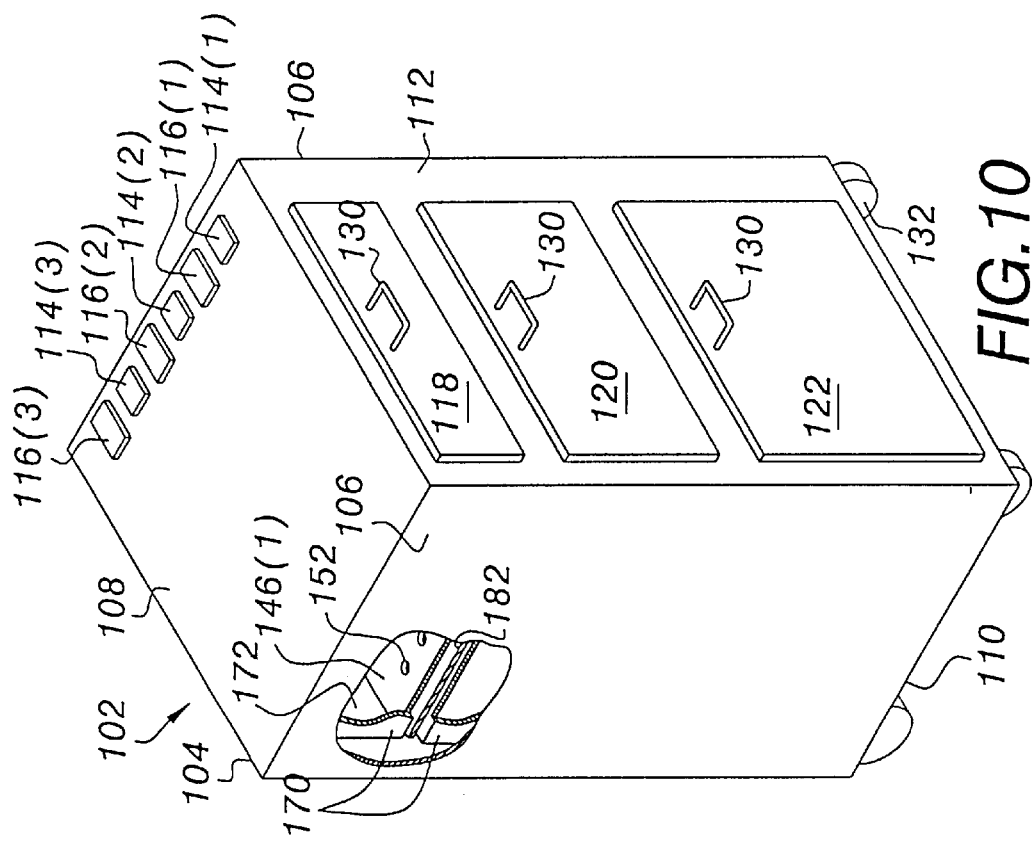
FIG. 10 is a view in perspective of an exemplary warming system having multiple compartments constructed into a single cabinet structure according to the present invention.
Figures 11, 12:
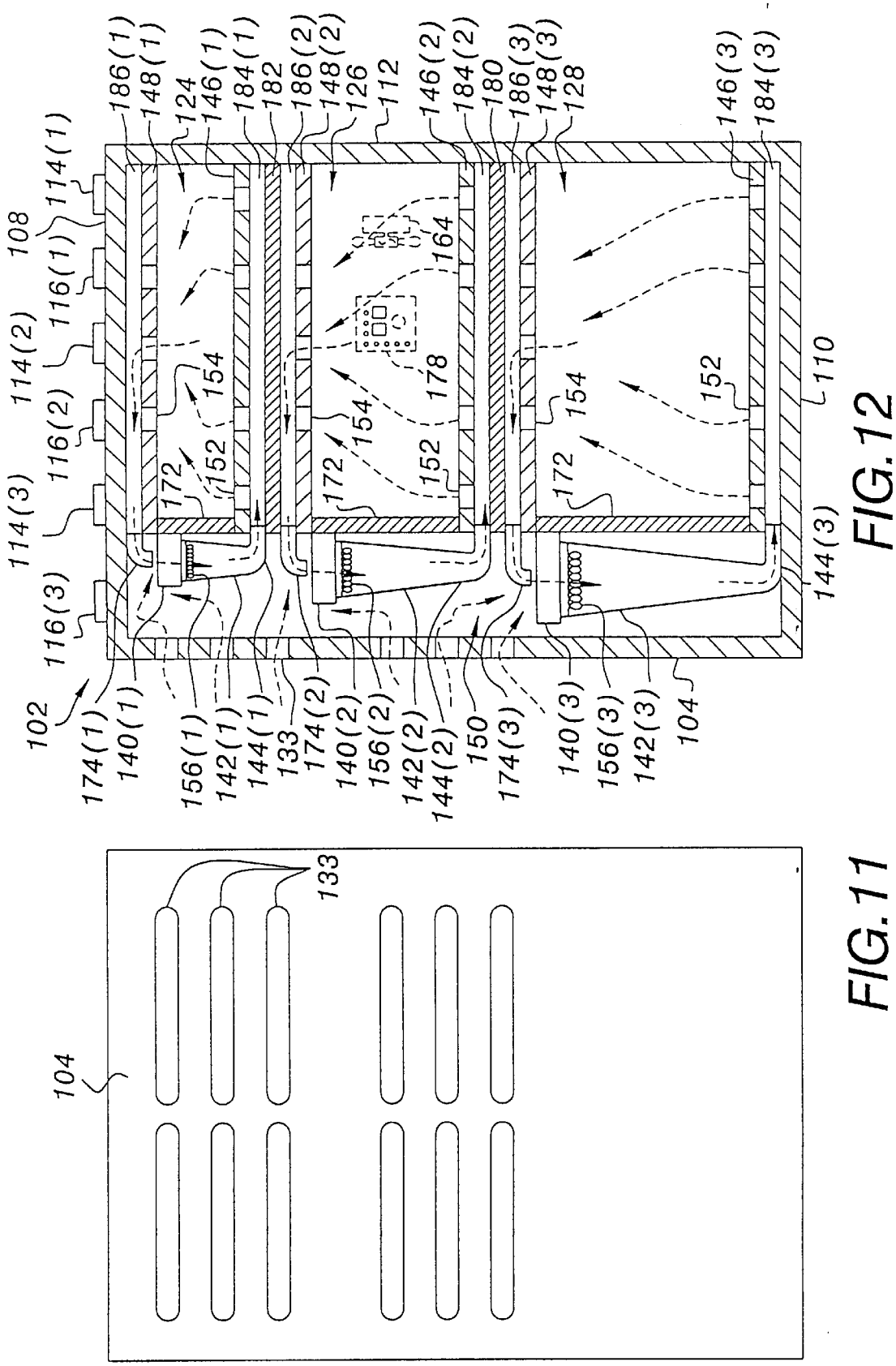
FIG. 11 is a view in elevation of a rear panel of the warming cabinet of FIG. 10 according to the present invention.
FIG. 12 is a side view in elevation and partial section of the warming cabinet of FIG. 10 diagrammatically illustrating air flow paths through warming cabinet compartments according to the present invention.

Alternatively, warming system 90 may be implemented as a single cabinet structure having multiple heating compartments. An exemplary surgical warming system or cabinet 102 having a single cabinet structure is illustrated in FIGS. 10–12. Specifically, cabinet 102 includes a rear panel 104, two substantially similar side panels 106, a top panel 108, a bottom panel 110 and a front panel 112. The top, side, front, rear and bottom panels are each substantially rectangular and define a cabinet interior wherein various medical or other items may be heated. Cabinet 102 includes a plurality of individual heating compartments 124, 126, 128 (FIG. 12), whereby each compartment is controlled by a corresponding process controller 116(1)–116(3), disposed on top panel 108, that is independent of process controllers associated with other compartments. Controllers 116(1)–116(3) are each substantially similar to controller 16 described above. Each compartment 124, 126, 128 typically includes a separate heating (i.e., temperature) range and may be set and maintained at a desired temperature independent of the other compartments. By way of example only, cabinet 102 includes three independent compartments disposed within the cabinet interior for heating medical or other items, however, the cabinet may include any number of independently controlled compartments.

Top panel 108 includes control switches 114(1)–114(3) and temperature controllers 116(1)–116(3) typically disposed toward a top panel edge (e.g., the top panel rightmost edge as viewed in FIG. 10) whereby a switch and controller correspond to each cabinet compartment to enable the compartments to be individually controlled. The switches and controllers may alternatively be disposed on the cabinet in any fashion capable of operating the cabinet. Switches 114(1)–114(3) enable power to a corresponding controller 116(1)–116(3) and fan 140(1)–140(3) disposed within the cabinet described below to commence heating of a particular compartment to a desired temperature. Controllers 116(1) –116(3) are each typically implemented by a microprocessor that displays a current temperature of an associated compartment and enables an operator to set a desired temperature for that compartment as described above. A main power switch 162 (FIG. 13) is typically disposed on a side panel 106 to enable operation of the entire cabinet. Top panel 108 may further include an intravenous support or pole (not shown) as described above to accommodate intravenous (IV) and/or irrigation fluid bags heated by warming cabinet 102 for application to patients. The intravenous pole mounted on the cabinet enhances efficiency by enabling immediate use of the warmed fluid since the pole and cabinet are in close proximity. Moreover, top panel 108 may include a lamp or other light source (not shown) as described above to illuminate the top panel such that an operator has sufficient light to transcribe information during a medical procedure. In addition, other items, typically utilized in an operating room, may be attached to cabinet 102 to reduce consumption of operating room space.

Front panel 112 includes a plurality of doors 118, 120, 122, that each enable access to respective cabinet compartments 124, 126, 128. Doors 118, 120, 122 are substantially rectangular and are disposed vertically adjacent each other with each door disposed within front panel 112 between side walls 170 of its corresponding compartment. The warmer cabinet compartments may vary in size or capacity as described above, whereby compartment 128 may include the largest capacity, while compartment 124 may include the smallest capacity. The varying compartment capacities enable different sized items to be heated whereby larger items may be disposed within compartment 128, while smaller items are typically disposed within compartment 124. However, items may be disposed in any compartment having sufficient capacity to accommodate that item. Similarly, doors 118, 120, 122 vary in size according to their corresponding compartments and have dimensions substantially similar to their corresponding compartment rear walls 172.

Doors 118, 120, 122 are preferably connected to front panel 112 via hinges disposed (not shown) toward their bottom edges that enable the doors to pivot downward toward bottom panel 110. Further, each door 118, 120, 122 includes a handle 130 disposed toward the center of the upper portion of the respective doors. Handles 130 are each preferably implemented by a C-shaped or bracket shaped handle that extends outward from an external surface of each door to provide sufficient space for an operator's hand to grip the handle and manipulate that door. Alternatively, handles 130 may be implemented by any handles capable of manipulating the doors. Doors 118, 120, 122 are typically manipulated to an open position to enable warming cabinet drawers described below to access the respective compartments whereby the drawers contain medical items to be heated by the warming cabinet.

Rear panel 104 (FIG. 11) is substantially rectangular as described above and includes dimensions substantially similar to front panel 112. A plurality of slots 133 are defined in the rear panel to permit air to enter the warming cabinet to be heated for maintaining the temperature of each compartment at an associated level as described below. Slots 133 are generally elliptical slots having their major axes extending along the shorter dimension of the rear panel whereby the major axes of the slots are substantially greater than the slot minor axes. Slots 133 are generally defined in rear panel 104 in groups of three rows (e.g., each row extends across the shorter dimension of the rear panel) with each row having two adjacent slots, whereby a group of slots is disposed coincident compartments 124, 126. However, rear panel 104 may include any quantity of slots whereby the slots may be of any shape or size and may be arranged in any fashion capable of enabling air to enter the warming cabinet.

Cabinet 102 may be either stationary or mobile wherein the cabinet may include wheels or casters 132, preferably having selectively actuable locking mechanisms. Wheels 132 may be attached to bottom panel 110 for enabling the cabinet to be transported to various locations. The surgical warming cabinet components are typically constructed of a suitably sturdy or rigid material, such as aluminum, but may be implemented by any material (e.g., metals, plastics, etc.) capable of accommodating the desired component function described herein.

Cabinet compartments 124, 126, 128 (FIG. 12) are disposed vertically adjacent each other with compartment 124 located proximate top panel 108 and compartment 128 located proximate bottom panel 110. Each compartment 124, 126, 128 includes side walls 170, rear wall 172, and respective floor and ceiling plates 146(1)–146(3) and 148(1)–148(3). The compartment side and rear walls 170, 172 and floor and ceiling plates 146(1)–146(3) and 148(1)–148(3), respectively, are substantially rectangular whereby side walls 170 of each compartment extend from front panel 112 toward rear panel 104. Side and rear walls 170, 172 of each compartment 124, 126, 128 are disposed about the peripheral edges of and between corresponding floor and ceiling plates 146(1)–146(3) and 148(1)–148(3), respectively, whereby the side and rear walls and floor and ceiling plates of each compartment define a compartment interior to heat medical or other items. Floor and ceiling plates 146(1)–146(3) and 148(1)–148(3) have substantially similar dimensions and include holes 152, 154 defined in the respective floor and ceiling plates to permit air flow through the compartments as described below. Further, a dividing wall 180 is disposed between compartments 126 and 128, while a dividing wall 182 is disposed between compartments 124 and 126. Dividing walls 180, 182 are substantially rectangular having dimensions substantially similar to respective floor and ceiling plates 146(1)–146(3) and 148(1)–148(3) whereby the dividing walls enable the compartments to reuse their own (e.g., recycled) air as described below.

Compartments 124, 126, 128 are each essentially in the form of a rectangular box whereby length and width dimensions of each compartment are similar, however, the length (e.g., compartment depth) and width (e.g., compartment height) of side and rear walls 170, 172, varies among the compartments to produce compartments of different sizes or capacities. The length and width dimensions of each compartment 124, 126, 128 are slightly less than the cabinet interior length and width dimensions such that a short distance resides between side walls 170 of each compartment and cabinet side panels 106, and between rear walls 172 of each compartment and cabinet rear panel 104. In addition, a slight distance resides between compartment 128 and bottom panel 110, between dividing wall 180 and compartments 126 and 128, between dividing wall 182 and compartments 124, 126 and between compartment 124 and top panel 108. The distances between compartment floor plates 146(1)–146(2) and the dividing walls, and between compartment floor plate 146(3) and the bottom panel form lower cavities 184(1)–184(3), while the distances between compartment ceiling plates 148(2)–148(3) and the dividing walls, and between compartment ceiling plate 148(1) and the top panel form upper cavities 186(1)–186(3). The lower and upper cavities are substantially rectangular and have dimensions substantially similar to respective floor and ceiling plates 146(1)–146(3) and 148(1)–148(3). The distance between compartment rear walls 172 and cabinet rear panel 104 serves as an air chamber 150 wherein outside air enters cabinet 102 via slots 133 defined in the cabinet rear panel as described above.

A heater in the form of a conventional fan 140(1)–140(3) with a corresponding heating coil 156(1)–156(3) is mounted on an exterior surface of rear wall 172 of each compartment 124, 126, 128 and forces air from air chamber 150 and a corresponding upper cavity 186(1)–186(3) over the heating coil to produce heated air that heats items disposed within that compartment. Air from respective upper cavities 186(1)–186(3) is received by corresponding fans 140(1)–140(3) via associated upper manifolds 174(1)–174(3). The upper manifolds are each disposed proximate an upper cavity 186(1)–186(3) and extend toward a corresponding fan 140(1)–140(3). The heated air flows through compartments 124, 126, 128 as described below whereby the heated air is recycled (e.g., re-used within that compartment) and mixed with outside air in various concentrations, depending upon the current compartment and desired temperatures, to control the compartment temperatures. Each compartment 124, 126, 128 further includes a thermocouple (not shown), substantially similar to the thermocouple described above, that measures the temperature within that compartment and sends a temperature signal to a corresponding controller 116(1)–116(3) described below. The thermocouple is typically disposed within each compartment 124, 126, 128 in one of the compartment side walls 170 at a height corresponding to approximately a middle height of the compartment.

Warming cabinet 102 heats a mixture of outside or make-up air and recycled air (e.g., air previously utilized within the particular compartments) and forces the heated air to flow proximate trays or drawers disposed within cabinet compartments 124, 126, 128 in order to heat the medical items contained within the drawers to desired temperatures. The trays or drawers are substantially similar to trays or drawers 34a–34d described above whereby a tray or drawer is utilized within each compartment 124, 126, 128 to heat various medical items in substantially the same manner described above. Alternatively, multiple drawers may be utilized within a single compartment that includes sufficient storage capacity to accommodate the drawers. The drawers are typically disposed on runners or tracks (not shown) mounted on an interior surface of side walls 170 of each compartment that enables the drawers to smoothly slide into and out of the compartments. This sliding action is similar to motions of drawers within common desks. The drawers may further be removed from the runners or tracks and replaced by other drawers of different configurations, or the individual drawer bins or receptacles may be replaced with other bins or receptacles as described above. Doors 118, 120, 122 are typically manipulated to an open position to enable access to the drawers within respective compartments 124, 126, 128.

Each cabinet compartment 124, 126, 128 individually heats and circulates air within that compartment and includes corresponding fan 140(1)–140(3) disposed on an exterior surface of respective compartment rear walls 172 toward the uppermost portion of the compartments. Fans 140(1)–140(3) draw air into the respective compartments from corresponding upper cavities 186(1)–186(3) (e.g., via respective upper manifolds 174(1)–174(3)) and air chamber 150, whereby air infiltrates the air chamber via rear panel slots 133 as described above. Ducts 142(1)–142(3) are disposed beneath corresponding fans 140(1)–140(3) and receive air driven by their corresponding fans. Ducts 142(1)–142(3) are each substantially trapezoidal (e.g., the ducts include a substantially trapezoidal cross-section) and extend from a corresponding fan 140(1)–140(3) toward an associated lower cavity 184(1)–184(3). The width of each duct gradually narrows from corresponding fans 140(1)–140(3) toward respective lower cavities 184(1)–184(3) whereby the ducts are similar in configuration to a funnel.

Ducts 142(1)–142(3) include respective heating coils 156(1)–156(3) disposed within the ducts toward a corresponding fan 140(1)–140(3) to heat the air. The ducts direct or funnel air over a corresponding heating coil 156(1)–156(3) and through an associated lower manifold 144(1)–144(3) disposed at a distal end of each duct. The lower manifolds respectively direct the air through associated lower cavities 184(1)–184(3) and into corresponding compartments via associated floor plates 146(1)–146(3) that are disposed above the respective lower cavities. Each floor plate 146(1)–146(3) is substantially similar to floor plate 46 (FIG. 4) described above having length and width dimensions substantially similar to its corresponding compartment length and width dimensions. Holes 152 are typically arranged through respective plates 146(1)–146(3) as described above to encompass the floor plate surface and enable heated air from corresponding lower cavities 184(1)–184(3) to enter associated compartments.

The heated air traverses compartments 124, 126, 128 and the drawers containing medical items disposed within those compartments to heat the items, and exits the compartments via corresponding ceiling plates 148(1)–148(3). Each ceiling plate 148(1)–148(3) is substantially similar to ceiling plate 48 (FIG. 5) described above and includes dimensions substantially similar to corresponding floor plates 146(1)–146(3). Holes 154 are typically arranged through respective ceiling plates 148(1)–148(3) as described above to encompass the ceiling plate surface and enable heated air to exit the compartments and enter corresponding upper cavities 186(1)–186(3).

The particular arrangements of holes 152, 154 within the respective floor and ceiling plates create a flume-like effect within each compartment to direct heated air toward the middle of the respective compartments as described above to enable the air to efficiently and evenly heat the items contained within compartment drawers. Air flow from ceiling plates 148(1)–148(3) is received in corresponding upper cavities 186(1)–186(3) disposed above ceiling plates 148(1)–148(3), whereby the air enters associated upper manifolds 174(1)–174(3) that direct the heated air back into fans 140(1)–140(3) within air chamber 150. Dividing walls 180 and 182 are respectively disposed between upper cavity 186(3) and lower cavity 184(2) (e.g., between compartments 126 and 128) and between upper cavity 186(2) and lower cavity 184(1) (e.g., between compartments 124 and 126) to enable each compartment to only reuse its air and prevent air from the various compartments from immediately entering a neighboring compartment. Dividing walls 180 and 182 have substantially similar dimensions as the floor and ceiling plates described above.

The air flow path through each compartment 124, 126, 128 is described with reference to the arrows (FIG. 12) indicating the flow path. Specifically, outside air infiltrates cabinet 102 via slots 133 defined in rear panel 104 and flows into air chamber 150 whereby the outside air mixes with heated air flowing from the compartments. Fans 140(1)–140(3) direct air from chamber 150 and upper manifolds 174(1)–174(3) through ducts 142(1)–142(3) whereby a corresponding heating coil 156(1)–156(3) disposed in the air flow paths within the ducts heats the air. The heated air is then directed into corresponding lower cavities 184(1)–184(3) via lower manifolds 144(1)–144(3) whereby the air traverses the floor plates into the associated compartments. The air flows within the compartments in a flume-like fashion described above through the compartment drawers to heat items contained within the drawers, and exits the compartments via respective ceiling plates 148(1)–148(3) into corresponding upper cavities 186(1)–186(3). Upper manifolds 174(1)–174(3) direct the air from upper cavities 186(1)–186

(3) back to fans 140(1)–140(3) within air chamber 150 to mix with fresh or make-up air and be recirculated into the compartments as described above to heat the medical items. The mixture of recycled and fresh air distributed to the compartments via fans 140(1)–140(3) is controlled in a conventional manner based on the compartment and desired temperatures in order to efficiently maintain the compartments at the desired temperatures.

Figure 13:
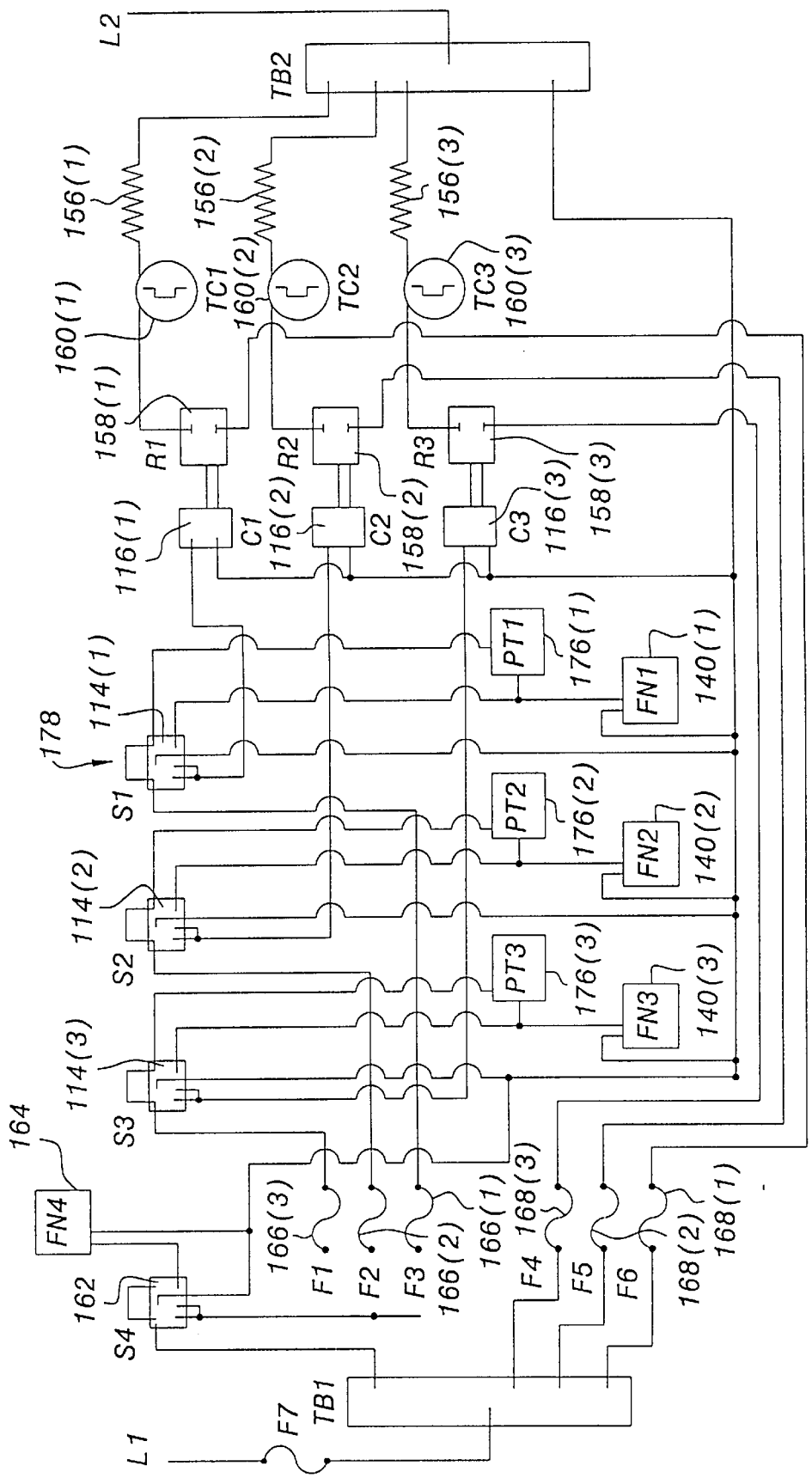
FIG. 13 is an electrical schematic diagram of an exemplary control circuit for the warming cabinet of FIG. 10 according to the present invention.

An exemplary control circuit 178 for controlling the cabinet compartments to heat medical items is illustrated in FIG. 13. Specifically, control circuit 178 is mounted on either cabinet side panel 106 (FIG. 12) in the space between the side panel and corresponding side walls 170 of the cabinet compartments, preferably coincident warmer cabinet compartment 126. A fan 164 is connected in series with power switch 162 that serves as the main power switch for the cabinet and enables operation of fan 164. Fan 164 is typically disposed proximate control circuit 178 to push fresh air from air chamber 150 over the control circuit components, preferably solid state relays 158(1)–158(3) described below, to maintain the components at an operable temperature. Further, fan 164 is utilized to circulate fresh or make-up air toward fans 140(1)–140(3) for mixture with recycled air received by the fans from the compartments.

Control circuit 178 further includes control switches 114(1)–114(3) corresponding to each compartment within cabinet 102. Switches 114(1)–114(3) are each connected in series with a corresponding compartment fan 140(1)–140(3), purge timer 176(1)–176(3) and temperature controller 116(1)–116(3) associated with a particular compartment. Switches 114(1)–114(3) are operator controlled and enable activation of a corresponding fan 140(1)–140(3) and controller 116(1)–116(3) whereby fans 140(1)–140(3) may be implemented for each compartment by conventional blowers or fans that direct air over a corresponding heating coil 156(1)–156(3) and through that compartment as described above. Purge timers 176(1)–176(3) enable activation of a corresponding compartment fan 140(1)–140(3) for approximately three to five minutes subsequent to switches 114(1)–114(3) disabling operation of that compartment to dissipate heat from and cool an associated heating coil 156(1)–156(3) in order to prevent damage to the cabinet from excessive heat as described above.

Temperature controllers 116(1)–116(3) are typically implemented by a microprocessor controller as described above and typically include a display to enable an operator to set a desired compartment temperature for a corresponding compartment via manipulation of display buttons that modify control parameters (e.g., temperature, mode of operation etc.) of the controller. Further, the displays of controllers 116(1)–116(3) provide the temperature of the compartment associated with that controller via signals received by the thermocouple disposed within that compartment as described above.

Controllers 116(1)–116(3) are each connected in series with a corresponding solid state relay 158(1)–158(3) that receives logic signals from an associated controller to close that relay and enable operation of a corresponding heating coil 156(1)–156(3) in accordance with the difference between the selected and existing compartment temperatures. Controllers 116(1)–116(3) essentially utilize PID control to adjust the current through corresponding heating coils 156(1)–156(3) via relays 158(1)–158(3) to maintain the compartments at a desired temperature based on the desired and current compartment temperatures. Heating coils 156(1)–156(3) are each disposed in series with a corresponding solid state relay 158(1)–158(3), and receive current from those relays to dissipate heat in order to heat the air within corresponding ducts 142(1)–142(3). High limit or overload switches 160(1)–160(3) are connected between and in series with corresponding solid state relays 158(1)–158(3) and heating coils 156(1)–156(3), and enter an open state to disable the heating coils by shunting excess current from the heating coils when the current exceeds a threshold level (e.g., a level that may damage the cabinet or circuit). Each switch 114(1)–114(3) and solid state relay 158(1)–158(3) is connected in series with a corresponding fuse 166(1)–166(3) and 168(1)–168(3), respectively, to protect the circuit from excess current. The various control circuit components are typically implemented via conventional or commercially available components and/or may be implemented by any circuitry based on the functional description of the circuit described above.

Operation of the warmer cabinet is described with reference to FIGS. 10, 12 and 13. Specifically, various medical items, such as intravenous or irrigation fluids, blood, instruments or drugs, are selected to be placed within warming cabinet 102. Main power switch 162 is enabled to power control circuit 178 and enable fan 164 to cool that circuit. A compartment 124, 126, 128 for receiving the items is selected based on the size of the items and the capacity of the compartment. A door 118, 120, 122 of the selected compartment is manipulated to an open position whereby a drawer (e.g., any of drawers 34a–34d described above) may be retrieved from or inserted (e.g., if no drawer is present) into that compartment. Further, an entire drawer may be replaced with another drawer, or individual drawer bins or receptacles may be replaced by other bins or receptacles to accommodate various medical items as described above. The medical items are inserted into the drawer as described above, and the drawer is placed into the selected compartment with that compartment door subsequently manipulated to a closed position. A control switch 114(1)–114(3) corresponding to the selected compartment is actuated to enable operation of a fan 140(1)–140(3) associated with that compartment to direct air over a corresponding heating coil 156(1)–156(3) and through the compartment as described above. A corresponding controller 116(1)–116(3) is manipulated via display buttons to set that controller to maintain the selected compartment at a desired temperature, typically in the approximate range of 86° F.–104° F. The controller further displays the current compartment temperature as measured by the thermocouple disposed within the selected compartment. When the medical items have attained the desired temperature, the drawer is retrieved from the compartment and the items are removed from the drawer for use in a medical or other procedure. This process may be repeated for remaining compartments within cabinet 102 to simultaneously heat various items to different temperatures. Moreover, cabinet compartments may be operated in any quantity either individually or in any combination to heat items contained within the compartments. In addition, the surgical warmer cabinet may be utilized in conjunction with an intravenous (IV) warming apparatus or a thermal treatment machine in substantially the same manner described above.

It will be appreciated that the embodiments described above and illustrated in the drawings represent only a few of the many ways of implementing a warming system and method for heating various items utilized in surgical procedures.

The warmer unit may be of any size or shape and may be constructed of any suitable materials. Air flow within the warmer unit may be directed toward items in any manner capable of heating the items via any suitable or conventional devices. The warmer unit may include any quantity (e.g., at least one) of compartments of any shape or size. The warmer unit door may be of any quantity (e.g., at least one), shape or size, may pivot in any fashion, and may be disposed anywhere on the warmer unit in any fashion capable of permitting access to the warmer unit compartment. The warmer unit door may be disposed on the warmer unit via hinges or any other mechanisms. Further, the warmer unit door may include any type of handle or other mechanism enabling opening and closing of the door, while the handle may be of any quantity (e.g., at least one), shape or size, and may be disposed on the door at any location and in any fashion. The door window may be of any shape or size, and may be disposed on the door at any location in any fashion, and may be constructed of polycarbonate or any other suitable and transparent material. Alternatively, the door may be utilized without a window, or with a translucent or opaque window.

The warmer unit power switch may be implemented by any conventional or other type of switch, button, relay or other device, and may be disposed anywhere on the warmer unit in any fashion. The controller holder may be of any quantity (e.g., at least one), shape or size, and may be disposed anywhere on the warmer unit. Alternatively, the controller may be directly embedded within the warmer unit at any location. The warmer unit rear panel slots may be disposed anywhere on the rear panel or warmer unit and may be of any quantity (e.g., at least one), shape or size. Any devices may be disposed on the warmer unit (e.g., intravenous pole, light, etc.) at any location to aid in activities prior, during or after surgical procedures.

The warmer units may be arranged in any fashion (e.g., vertically, horizontally, etc.), and may be of any quantity (e.g., at least one) to form a multiple unit warming system. The warmer unit slots and feet may be of any quantity (e.g., at least one), shape or size, and may be disposed anywhere on the warmer unit in any fashion to securely arrange the warmer units. Further, the warmer units may include any type of fastening or securing mechanisms to secure the warmer units in any configuration. The warmer unit feet may further include wheels, rollers or other devices to enable warmer units to be transportable, while the transport devices may include locking mechanisms to maintain a warmer unit in place.

The warming cabinet may be of any shape or size and may be constructed of any suitable materials, while the warming cabinet compartments may be of any quantity (e.g., at least one), shape or size. Air flow within the warming cabinet compartments may be directed toward items in any manner capable of heating the items via any conventional or suitable devices. The warming cabinet compartments may be arranged in any fashion (e.g., vertically, horizontally, etc.) such that any sized compartment may be disposed anywhere on the cabinet. The warming cabinet doors may be of any quantity (e.g., at least one), shape or size, may pivot in any fashion, and may be disposed anywhere on the warming cabinet in any fashion capable of permitting access to the compartments. The warming cabinet doors may be disposed on the warming unit via hinges or any other mechanisms. Further, the warming cabinet doors may include any types of handles or other mechanisms enabling opening and closing of the doors, while the handles may be of any quantity (e.g., at least one), shape or size, and may be disposed on the doors at any location and in any fashion. The doors may include a window of any shape or size that may be disposed on the door at any location in any fashion. The window may be constructed of polycarbonate or any other suitable materials.

The power switches of the warming cabinet may be implemented by any conventional or other types of switches, buttons, relays or other devices, and may be disposed anywhere on the warming cabinet in any fashion. The controllers may similarly be disposed anywhere on the warming cabinet. The warming cabinet rear panel slots may be disposed anywhere on the rear panel or warming cabinet and may be of any quantity (e.g., at least one), shape or size. Any devices may be disposed on the warming cabinet (e.g., intravenous pole, light, etc.) at any location to aid in activities prior, during or after surgical procedures.

The manifolds and ducts of the warmer unit or warming cabinet may be implemented by any conventional or other types of manifolds, ducts, tubes or other devices capable of directing air flow. The manifolds and ducts may be disposed in any manner proximate or within the warmer unit or warming cabinet to recycle air through the warmer unit or warming cabinet compartments. The manifolds and ducts may be of any quantity (e.g., at least one), shape or size, and may be constructed of any suitable materials. The heating coils of the warmer unit or warming cabinet may be implemented by any conventional or other type of heating element or device capable of heating air, and may be disposed within the warmer unit or warming cabinet at any location. Further, the air within the warmer unit or warming cabinet may be heated by any conventional or other type of heating device to warm the items.

The ceiling and floor plates of the warmer unit or warming cabinet may be of any quantity (e.g., at least one), shape or size, may be disposed in any fashion within the warmer unit or warming cabinet compartments to direct air flow, and may be constructed of any suitable materials. The floor and ceiling plates may include any quantity (e.g., at least one) of holes of any shape or size arranged in any configuration to direct air within the warmer unit or warming cabinet compartments.

The trays or drawers described above and utilized within the warmer unit or warming cabinet compartments may be of any quantity (e.g., at least one), shape or size, may be implemented by any tray, drawer or other device capable of holding items within the compartment, and may be constructed of any suitable materials. The trays or drawers may include bins, receptacles or other containers of any quantity (e.g., at least one), shape or size to contain any items at any desired orientations. The trays or drawers may be placed within and removed from the warmer unit or warming cabinet compartments via any suitable mechanisms (e.g., tracks, runners, rollers, etc.). Further, the trays or drawers may accommodate any items for heating. Moreover, the trays or drawers may be removably secured to the warmer unit or warming cabinet compartments and be interchanged with other drawers having different configurations to accommodate various items (e.g. instruments, blankets, etc.). In addition, the bins or receptacles of the trays or drawers may be interchangeable such that the trays or drawers may include bins or receptacles of various configurations to accommodate various quantities of items, varying item orientations (e.g., maintaining IV solution bags in an upright position) or items of different types or sizes. The trays or drawers may include any quantity or combination of fixed and/or interchangeable bins or receptacles.

The mesh material of the trays or drawers may be implemented by wire, rope or other material that enables air flow through the drawers and can withstand the compartment temperature. The mesh material may be attached to the trays or drawers at any suitable locations via any conventional or other fastening techniques. The longitudinal and transverse dividers of drawer 34c may be of any quantity, shape or size, may be implemented by any type of divider that partitions the drawer interior, and may be constructed of any suitable materials. These dividers may be attached to the drawer at any suitable locations via any conventional or other fastening techniques. The transverse and longitudinal dividers may include any quantity of wire members arranged in any fashion, whereby the wire members may include any quantity of wires arranged in any fashion. The divider wire members may be implemented by any wire, rope, cable, string or other line of any size or cross-sectional shape that can withstand the compartment temperature.

The floor of drawers 34c and 34d may be implemented by any material or pattern enabling heated air to infiltrate the drawer and heat items contained therein, while the support wire members and peripheral wire members of those drawers may be implemented by any wire, rope, cable, string or other line of any size or cross-sectional shape that can withstand the compartment temperature. The support and peripheral wire members may be of any quantity, and may be disposed on the drawers in any fashion. The support bars, posts and other components (e.g., upper frame, floor, etc.) of the drawers may be of any shape or size, may be constructed of any suitable materials and may be disposed on the drawers or arranged in any fashion.

The longitudinal and transverse dividers of drawer 34d may be of any quantity, shape or size, may be implemented by any type of divider that partitions the drawer interior, and may be constructed of any suitable materials. These dividers may be attached to the partition frame at any suitable locations via any conventional or other fastening techniques. The partition frame may be placed in slidable relation with the drawer via any conventional or other mechanisms enabling partition frame motion. The function of the partition frame may alternatively be implemented by any device that can configure the drawer interior into a large single receptacle or several individual receptacles. Drawer 34d may include any configurations having a single receptacle of any shape or size, or any quantity of individual receptacles of any shape or size. The mesh material may be disposed through any quantity of partition frame spaces to form any quantity of individual receptacles. The partition frame may be positioned at any location between the upper frame and floor to form receptacles having any desired storage capacity.

The control circuits may be disposed within the warmer unit and warming cabinet at any suitable locations. The components of the control circuits may be implemented by any conventional components or other circuitry capable of performing the functions described herein. The thermocouple may be implemented by any conventional or other type of temperature sensor or other device capable of measuring temperature, and may be disposed at any location within the warmer unit or warming cabinet compartments. The controllers may be implemented by any conventional or other microprocessor, controller or other circuitry capable or controlling the heating coils. The purge timers may be implemented by any conventional timers or other circuitry, and may be set to enable the fans for any desired time interval. The power receptacles may be implemented by any receptacles capable of interfacing a detachable power cord, or the circuit may include a power cord to receive power from a common wall outlet jack. The fans may be implemented by any conventional or other types of blowers, fans or other devices capable of directing air. The solid state relays may be implemented by any conventional or other type of switches, relays or other devices capable of controlling current/voltage to the heating coils.

The warmer unit or warming cabinet may be programmed to maintain compartments at any desired temperatures, may be utilized to heat various items for varying applications, and are not limited to the applications described herein. Further, the warmer unit and warming cabinet may operate without recycling air by directing outside air through the compartments in substantially the same manner described above. The mixing of recycled and outside air may be accomplished in any suitable or conventional manners. For example, valves may be utilized within the manifolds or ducts to control mixing, the speed of the fan directing recycled air back into a compartment may be controlled, or the rear panel slots may be covered or controlled to limit the amount of outside air entering the system. The warmer units of a multiple unit warming system may be operated either individually or in any combination or quantity to heat items contained within the units. Similarly, the compartments of the warming cabinet may be operated either individually or in any quantity or combination to heat items contained within the compartments. The warmer unit or warming cabinet may be operated via any suitable steps in any manner whereby the steps described above for operation of these systems may be selectively performed or performed in any desired sequence. The warmer unit or warming cabinet may be utilized without the trays or drawers by placing items within the warmer unit or warming cabinet compartments. Further, the warmer unit or warming cabinet may be utilized with various other medical apparatus to warm items prior to use within those apparatus, such as intravenous warming systems, thermal treatment machines, etc.

From the foregoing description it will be appreciated that the invention makes available a novel warming system and method for heating various items utilized in surgical procedures wherein multiple individually controlled compartments of the system simultaneously maintain various items at different temperatures.

Having described preferred embodiments of a new and improved warming system and method for heating various items utilized in surgical procedures, it is believed that other modifications, variations and changes will be suggested to those skilled in the art in view of the teaching set forth herein. It is therefore to be understood that all such variations, modifications and changes are believed to fall within the scope of the present invention as defined by the appended claims.

What is claimed is:

1. A warming system for heating medical items to desired temperatures within an approximate range of 86° F.–104° F. prior to using said medical items within medical procedures comprising:

a plurality of individually controllable stand-alone warmer units for heating said medical items to said desired temperatures, wherein each said warmer unit maintains a corresponding desired temperature and includes:

a housing;

a compartment disposed within said housing to receive at least one medical item to be heated;

a heater disposed proximate said compartment to direct heated air into said compartment to heat said compartment and said at least one medical item contained within said compartment;

a temperature sensor disposed within said compartment to measure temperature in said compartment; and a controller including at least one input device manipulable externally of said housing by a user to facilitate entry of said corresponding desired temperature within said range for said compartment and, in response to entry of said corresponding desired temperature, to control said heater to heat said compartment to the entered desired temperature based on the temperature measured by said temperature sensor;

wherein said warming system simultaneously heats said medical items contained within said warmer units to the respective desired temperatures entered for said warmer units, and wherein at least two of said warmer units heat said medical items to different desired temperatures.

2. The system of claim 1 wherein said heater includes:

a heating element; and a fan to direct air across said heating element to produce said heated air and to direct said heated air into said compartment to heat said compartment and said at least one medical item contained within said compartment.

3. The system of claim 1 wherein said compartment includes:

a floor plate disposed toward a compartment lower portion and having a first series of openings defined therein to permit said heated air to enter said compartment; and a ceiling plate disposed toward a compartment upper portion and having a second series of openings defined therein to permit said heated air to exit said compartment;

wherein said first and second series of openings are defined in said respective floor and ceiling plates in particular arrangements to direct said heated air to flow in a converging fashion within said compartment toward said at least one medical item.

4. The system of claim 2 wherein said each warmer unit further includes:

a plurality of slots to enable outside air to enter that warmer unit, wherein said fan receives a mixture of said outside air and said heated air flowing from said compartment and directs said mixture across said heating element into said compartment.

5. The system of claim 1 wherein said each warmer unit further includes:

a receptacle including a plurality of containers for receiving and securing said at least one medical item within said compartment, wherein said receptacle is disposed in sliding relation with said compartment to enable said receptacle to be placed within and removed from said compartment.

6. The system of claim 5 wherein at least one of said plurality of containers is removably secured to said receptacle and interchangeable.

7. The system of claim 5 wherein said receptacle includes an interior partitioned into said plurality of containers with each said container including sufficient storage capacity to contain said at least one medical item in an upright position.

8. The system of claim 1 wherein each said warmer unit further includes:

a receptacle including a selectively adjustable interior configuration for receiving and securing said at least one medical item within said compartment, wherein said receptacle interior configuration is selectively adjustable between a single container having a first storage capacity and a plurality of individual containers each having a second storage capacity less than said first storage capacity for containing said at least one medical object within said receptacle.

9. A warming system for heating items to desired temperatures prior to use within medical procedures comprising:

a plurality of individually controllable warmer units arranged in stacked relation for heating items to desired temperatures, wherein each said warmer unit maintains a corresponding desired temperature assigned to that warmer unit and includes:

a compartment disposed within that warmer unit to receive at least one item to be heated;

a heater disposed proximate said compartment to direct heated air into said compartment to heat said compartment and said at least one item contained within said compartment;

a temperature sensor disposed within said compartment to measure temperature of said compartment;

a controller to control said heater to heat said compartment to the temperature assigned to that warmer unit based on the temperature measured by said temperature sensor;

at least one fastening member disposed on an exterior surface of that warmer unit to interface an adjacent warmer unit; and at least one receptacle to receive said at least one fastening member of another warmer unit and facilitate securing of said warmer units in stacked relation;

wherein said warming system simultaneously heats items contained within said warmer units to the respective temperatures assigned to said warmer units.

10. The system of claim 1 wherein at least one warmer unit compartment includes a support structure to contain a medical solution.

11. A warming cabinet for heating medical items to desired temperatures within an approximate range of 86° F.–104° F. prior to using said medical items within medical procedures comprising:

a plurality of individually controllable compartments for heating said medical items to said desired temperatures, wherein each said compartment maintains a corresponding desired temperature and includes:

a heater to direct heated air into that compartment to heat that compartment and at least one medical item contained within that compartment;

an air intake to supply ambient air from outside said warming cabinet to said heater;

an air recycling unit to direct re-cycled air from that compartment back to said heater to be heated as necessary;

a guide to direct heated ambient air and re-cycled air from said heater to that compartment;

a temperature sensor disposed within that compartment to measure temperature in that compartment; and a controller to facilitate entry of a desired temperature for that compartment and to control said heater to heat that compartment to the entered desired temperature based on the temperature measured by said temperature sensor;

wherein said warming cabinet simultaneously heats medical items contained within said compartments to the respective desired temperatures entered for said compartments.

12. The cabinet of claim 11 wherein said heater includes:

a heating element; and a fan to direct air across said heating element to produce said heated air and to direct said heated air into that compartment via said guide to heat that compartment and said at least one medical item contained within that compartment.

13. The cabinet of claim 11 wherein said each compartment includes:

a floor plate disposed toward a compartment lower portion and having a first series of openings defined therein to permit said heated air to enter that compartment; and a ceiling plate disposed toward a compartment upper portion and having a second series of openings defined therein to permit said heated air to exit that compartment;

wherein said first and second series of openings are defined in said respective floor and ceiling plates in particular arrangements to direct said heated air to flow in a converging fashion within that compartment toward said at least one medical item.

14. The cabinet of claim 12 wherein said air intake includes a plurality of slots to enable said outside air to enter said warming cabinet, wherein said fan of each compartment receives a mixture of said outside air and said re-cycled air flowing from that compartment and directs said mixture across a corresponding heating element into that compartment.

15. The cabinet of claim 11 wherein said each compartment further includes:

a receptacle including a plurality of containers for receiving and securing said at least one medical item within that compartment, wherein said receptacle is disposed in sliding relation with that compartment to enable said receptacle to be placed within and removed from that compartment.

16. The cabinet of claim 15 wherein at least one of said plurality of containers is removably secured to said receptacle and interchangeable.

17. The cabinet of claim 15 wherein said receptacle includes an interior partitioned into said plurality of containers with each said container including sufficient storage capacity to contain said at least one medical item in an upright position.

18. The cabinet of claim 11 wherein said each compartment further includes:

a receptacle including a selectively adjustable interior configuration for receiving and securing said at least one medical item within that compartment, wherein said receptacle interior configuration is selectively adjustable between a single container having a first storage capacity and a plurality of individual containers each having a second storage capacity less than said first storage capacity for containing said at least one medical object within said receptacle.

19. The cabinet of claim 11 wherein at least one compartment includes a support structure to contain a medical solution.

20. In a warming system having a plurality of individually controllable stand-alone warmer units wherein each warmer unit includes a housing, a warmer unit compartment for receiving at least one medical item, a heater for heating that compartment, a temperature sensor for measuring a temperature of that compartment and a controller to control the heater, a method of heating medical items to desired temperatures within an approximate range of 86° F.–104° F. prior to using said medical items within medical procedures comprising the steps of:

(a) simultaneously heating said medical items to said desired temperatures within at least two of said stand-alone warmer units, wherein step (a) further includes:

(a.1) disposing at least one medical item to be heated within the compartments of said at least two warmer units;

(a.2) entering into the respective controllers of said at least two warmer units, via controller input devices manipulable externally of said respective warmer unit housings by a user, a desired temperature within said range corresponding to that warmer unit;

(a.3) directing heated air into the compartments of said at least two warmer units, via the respective heaters, to heat the compartments and said at least one medical item contained within each of the compartments;

(a.4) measuring the temperature of the compartments of said at least two warmer units via the respective temperature sensors; and (a.5) in response to entry of said corresponding desired temperatures, controlling the heaters of said at least two warmer units, via the respective controllers, to simultaneously heat the compartments to their corresponding desired temperatures based on the compartment temperatures measured by the corresponding temperature sensors, wherein at least two of said warmer units heat the compartments to different corresponding desired temperatures.

21. The method of claim 20 wherein step (a.3) further includes:

(a.3.1) directing air across heating elements of the respective heaters of said at least two warmer units to produce the heated air and directing the heated air into the compartments of said at least two warmer units to heat the compartments and said at least one medical item contained within each of the compartments.

22. The method of claim 20 wherein each warmer unit compartment includes:

a floor plate disposed toward a compartment lower portion and having a first series of openings defined therein to permit the heated air to enter that warmer unit compartment; and a ceiling plate disposed toward a compartment upper portion and having a second series of openings defined therein to permit the heated air to exit that warmer unit compartment;

wherein said first and second series of openings within said floor and ceiling plates are configured in a particular arrangement to direct the heated air to flow in a converging fashion within that warmer unit compartment; and step (a.3) further includes:

(a.3.1) directing the heated air to flow in a converging fashion within the compartments of said at least two warmer units toward said at least one medical item contained within each of the compartments via said configuration of said first and second openings.

23. The method of claim 21 wherein step (a.3.1) further includes:

(a.3.1.1) mixing heated air flowing from the compartments of said at least two warmer units with outside air to produce respective air mixtures and directing each air mixture across the heating element of the corresponding heater and into the corresponding compartment.

24. The method of claim 20 wherein each said warmer unit compartment includes a receptacle having a plurality of containers wherein said receptacle is disposed in sliding relation with that warmer unit compartment, and step (a.1) further includes:

(a.1.1) disposing said at least one medical item within said receptacles of said at least two warmer units; and (a.1.2) sliding said receptacles within the compartments of said at least two warmer units to secure said at least one medical item within the compartments.

25. The method of claim 24 wherein at least one of said plurality of containers is removably secured to said receptacle and interchangeable, and step (a.1.1) further includes:
 (a.1.1.1) replacing at least one interchangeable container of said receptacle within at least one of said warmer units to contain said at least one medical item.

26. The method of claim 24 wherein step (a.1.1) further includes:
 (a.1.1.1) partitioning an interior of said receptacle within at least one of said warmer units into said plurality of containers with each said container including sufficient storage capacity to contain said at least one medical item in an upright position.

27. The method of claim 20 wherein each said warmer unit compartment includes a receptacle including a selectively adjustable interior configuration for receiving and securing said at least one medical item within that compartment, and step (a.1) further includes:
 (a.1.1) selectively adjusting said interior configurations of said receptacles within said at least two warmer units;
 (a.1.2) disposing said at least one medical item within said receptacles of said at least two warmer units; and
 (a.1.3) sliding said receptacles within the compartments of said at least two warmer units to secure said at least one medical item within the compartments.

28. In a warming system having a plurality of individually controllable warmer units wherein each warmer unit includes a warmer unit compartment for receiving at least one item, a heater for heating that compartment, a temperature sensor for measuring a temperature of that compartment, a controller to control the heater, at least one fastening member disposed on an exterior surface of that warmer unit to interface an adjacent warmer unit and at least one receptacle to receive at least one fastening member of another warmer unit, a method of heating items to desired temperatures prior to use within medical procedures comprising the steps of:
 (a) arranging said warmer units in stacked relation by interfacing adjacent warmer units via said at least one fastening member and said at least one receptacle;
 (b) simultaneously heating said items to said desired temperatures within at least two of said warmer units, wherein step (b) further includes:
  (b.1) disposing at least one item to be heated within the compartments of said at least two warmer units;
  (b.2) assigning a desired temperature to each of said at least two warmer units;
  (b.3) directing heated air into the compartments of said at least two warmer units, via the respective heaters, to heat the compartments and said at least one item contained within each of the compartments;
  (b.4) measuring the temperature of the compartments of said at least two warmer units via the respective temperature sensors; and
  (b.5) controlling the heaters of said at least two warmer units, via the respective controllers, to simultaneously heat the compartments to their corresponding assigned temperatures based on the compartment temperatures measured by the corresponding temperature sensors.

29. The method of claim 20 wherein step (a.1) further includes:
 (a.1.1) disposing a medical solution within the compartment of at least one warmer unit.

30. In a warming cabinet having a plurality of individually controllable compartments wherein each warming cabinet compartment includes a heater for heating that compartment, a temperature sensor for measuring a temperature of that compartment and a controller to control the heater, a method of heating medical items to desired temperatures within an approximate range of 86° F.–104° F. prior to using said medical items within medical procedures comprising the steps of:
 (a) simultaneously heating said medical items to said desired temperatures within at least two warming cabinet compartments, wherein step (a) further includes:
  (a.1) disposing at least one medical item to be heated within said at least two warming cabinet compartments;
  (a.2) entering into the respective controllers of said at least two warming cabinet compartments a desired temperature corresponding to that compartment;
  (a.3) directing heated air into said at least two warming cabinet compartments, via the respective heaters, to heat the compartments and said at least one medical item contained within each of the compartments;
  (a.4) supplying ambient air from outside said warming cabinet to the respective heaters of said at least two warming cabinet compartments;
  (a.5) directing re-cycled air from said at least two warming cabinet compartments back to their corresponding heaters to be heated as necessary;
  (a.6) directing heated ambient air and re-cycled air to said at least two warming cabinet compartments from their corresponding heaters;
  (a.7) measuring the temperature of said at least two warming cabinet compartments via the respective temperature sensors; and
  (a.8) controlling the heaters of said at least two warming cabinet compartments, via the respective controllers, to simultaneously heat the compartments to their corresponding desired temperatures based on the compartment temperatures measured by the corresponding temperature sensors.

31. The method of claim 30 wherein step (a.3) further includes:
 (a.3.1) directing air across heating elements of the respective heaters of said at least two warming cabinet compartments to produce the heated air and directing the heated air into said at least two warming cabinet compartments to heat the compartments and said at least one medical item contained within each of the compartments.

32. The method of claim 30 wherein each warming cabinet compartment includes:
 a floor plate disposed toward a compartment lower portion and having a first series of openings defined therein to permit the heated air to enter that warming cabinet compartment; and
 a ceiling plate disposed toward a compartment upper portion and having a second series of openings defined therein to permit the heated air to exit that warming cabinet compartment;
 wherein said first and second series of openings within said floor and ceiling plates are configured in a particular arrangement to direct the heated air to flow in a converging fashion within that warming cabinet compartment; and
 step (a.3) further includes:
  (a.3.1) directing the heated air to flow in a converging fashion within said at least two warming cabinet compartments toward said at least one medical item contained within each of the compartments via said configuration of said first and second openings.

33. The method of claim 30 wherein each said warming cabinet compartment includes a receptacle having a plurality of containers wherein said receptacle is disposed in sliding relation with that warming cabinet compartment, and step (a.1) further includes:
(a.1.1) disposing said at least one medical item within said receptacles of said at least two warming cabinet compartments; and
(a.1.2) sliding said receptacles within said at least two warming cabinet compartments to secure said at least one medical item within the compartments.

34. The method of claim 33 wherein at least one of said plurality of containers is removably secured to said receptacle and interchangeable, and step (a.1.1) further includes:
(a.1.1.1) replacing at least one interchangeable container of said receptacle within at least one of said warming cabinet compartments to contain said at least one medical item.

35. The method of claim 33 wherein step (a.1.1) further includes:
(a.1.1.1) partitioning an interior of said receptacle within at least one of said warming cabinet compartments into said plurality of containers with each said container including sufficient storage capacity to contain said at least one medical item in an upright position.

36. The method of claim 30 wherein each said warming cabinet compartment includes a receptacle including a selectively adjustable interior configuration for receiving and securing said at least one medical item within that warming cabinet compartment, and step (a.1) further includes:
(a.1.1) selectively adjusting said interior configurations of said receptacles within said at least two warming cabinet compartments;
(a.1.2) disposing said at least one medical item within said receptacles of said at least two warming cabinet compartments; and
(a.1.3) sliding said receptacles within said at least two warming cabinet compartments to secure said at least one medical item within the compartments.

37. The method of claim 30 wherein step (a.1) further includes:
(a.1.1) disposing a medical solution within at least one warming cabinet compartment.

38. A warming system for heating medical items to desired temperatures within an approximate range of 86° F.–104° F. prior to using said medical items within medical procedures comprising:
a housing;
a compartment disposed within said housing to receive at least one medical item to be heated;
a heater disposed proximate said compartment to direct heated air into said compartment to heat said compartment and said at least one medical item contained within said compartment;
an air intake to supply ambient air from outside said warming system to said heater;
an air recycling unit to direct re-cycled air from said compartment back to said heater to be heated as necessary;
a guide to direct heated ambient air and re-cycled air from said heater to said compartment;
a temperature sensor disposed within said compartment to measure temperature in said compartment; and
a controller including at least one input device manipulable externally of said housing by a user to facilitate entry of a desired temperature within said range for said compartment and, in response to entry of said corresponding desired temperature, to control said heater to heat said compartment to the entered desired temperature based on the temperature measured by said temperature sensor.

39. The warming system of claim 38 further including:
a receptacle including a plurality of containers for receiving and securing said at least one medical item within said compartment, wherein said receptacle is disposed in sliding relation with said compartment to enable said receptacle to be placed within and removed from said compartment.

40. The warming system of claim 39 wherein at least one of said plurality of containers is removably secured to said receptacle and interchangeable.

41. The warming system of claim 39 wherein said receptacle includes an interior partitioned into said plurality of containers with each said container including sufficient storage capacity to contain said at least one medical item in an upright position.

42. The warming system of claim 38 further including:
a receptacle including a selectively adjustable interior configuration for receiving and securing said at least one medical item within said compartment, wherein said receptacle interior configuration is selectively adjustable between a single container having a first storage capacity and a plurality of individual containers each having a second storage capacity less than said first storage capacity for containing said at least one medical object within said receptacle.

43. In a warming system having a housing, a compartment disposed within said housing for receiving at least one medical item, a heater for heating said compartment, a temperature sensor for measuring a temperature of said compartment and a controller to control the heater, a method of heating medical items to desired temperatures within an approximate range of 86° F.–104° F. prior to using said medical items within medical procedures comprising the steps of:
(a) heating said medical items to said desired temperatures within said warming system compartment, wherein step (a) further includes:
(a.1) disposing at least one medical item to be heated within said compartment;
(a.2) entering into the controller, via at least one controller input device manipulable externally of said housing by a user, a desired temperature for the compartment within said range;
(a.3) directing heated air into the compartment, via the heater, to heat the compartment and said at least one medical item contained within the compartment;
(a.4) supplying ambient air from outside said warming system to the heater;
(a.5) directing re-cycled air from said compartment back to the heater to be heated as necessary;
(a.6) directing heated ambient air and re-cycled air from the heater to the compartment.
(a.7) measuring the temperature of said compartment via the temperature sensor; and
(a.8) in response to entry of said corresponding desired temperature, controlling the heater, via the controller, to heat the compartment to the entered desired temperature based on the compartment temperature measured by the temperature sensor.

44. The method of claim 43 wherein said warming system further includes a receptacle having a plurality of containers wherein said receptacle is disposed in sliding relation with the compartment, and step (a.1) further includes:

(a.1.1) disposing said at least one medical item within said receptacle; and (a.1.2) sliding said receptacle within said compartment to secure said at least one medical item within the compartment.

45. The method of claim 44 wherein at least one of said plurality of containers is removably secured to said receptacle and interchangeable, and step (a.1.1) further includes:

(a.1.1.1) replacing at least one interchangeable container of said receptacle to contain said at least one medical item.

46. The method of claim 44 wherein step (a.1.1) further includes:

(a.1.1.1) partitioning an interior of said receptacle into said plurality of containers with each said container including sufficient storage capacity to contain said at least one medical item in an upright position.

47. The method of claim 43 wherein said warming system further includes a receptacle having a selectively adjustable interior configuration for receiving and securing said at least one medical item within the compartment, and step (a.1) further includes:

(a.1.1) selectively adjusting said interior configuration of said receptacle;

(a.1.2) disposing said at least one medical item within said receptacle; and (a.1.3) sliding said receptacle within said compartment to secure said at least one medical item within the compartment.

* * * * *